US009445833B2

(12) United States Patent
Akagane

(10) Patent No.: US 9,445,833 B2
(45) Date of Patent: Sep. 20, 2016

(54) ULTRASONIC PROBE AND ULTRASONIC TREATMENT APPARATUS

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/939,766

(22) Filed: Nov. 12, 2015

(65) Prior Publication Data

US 2016/0058465 A1 Mar. 3, 2016

Related U.S. Application Data

(63) Continuation of application No. PCT/JP2014/065132, filed on Jun. 6, 2014.

(30) Foreign Application Priority Data

Jun. 7, 2013 (JP) ................................ 2013-121019

(51) Int. Cl.

| | |
|---|---|
| ***A61B 17/32*** | (2006.01) |
| *A61B 17/28* | (2006.01) |
| *A61B 17/29* | (2006.01) |

(52) U.S. Cl.

CPC .................. *A61B 17/320092* (2013.01); *A61B 17/320068* (2013.01); *A61B 2017/2825* (2013.01); *A61B 2017/2945* (2013.01); *A61B 2017/320072* (2013.01)

(58) Field of Classification Search

CPC .............. A61B 8/4477; A61B 8/4483; A61B 17/320068; A61B 17/320092; A61B 2017/2825; A61B 2017/2945; A61B 2017/320072

See application file for complete search history.

(56) References Cited

U.S. PATENT DOCUMENTS 5,413,107 A * 5/1995 Oakley .................... A61B 8/12 600/463

6,283,981 B1 9/2001 Beaupre (Continued)

FOREIGN PATENT DOCUMENTS

| | | |
|---|---|---|
| JP | 2000-070279 A | 3/2000 |
| JP | 2009-160404 A | 7/2009 |
| JP | 2011-500161 A | 1/2011 |

OTHER PUBLICATIONS

Sep. 2, 2014 Search Report issued in International Patent Application No. PCT/JP2014/065132.

(Continued)

*Primary Examiner* — Gregory Anderson
*Assistant Examiner* — Christina Lauer
(74) *Attorney, Agent, or Firm* — Oliff PLC

(57) ABSTRACT

An ultrasonic probe includes a probe bend portion bending relative to a probe main body portion in a first bend direction and a second bend direction with a center of gravity being located on a first bend direction side with respect to a longitudinal axis. In the probe bend portion, a cross-sectional shape in a cross section perpendicular to a first perpendicular direction and a second perpendicular direction varies continuously along the first perpendicular direction and the second perpendicular direction with a cross-sectional center of gravity in the cross section perpendicular to the first perpendicular direction and the second perpendicular direction lying toward the second bend direction, as it is from the first perpendicular direction toward the second perpendicular direction.

6 Claims, 14 Drawing Sheets

(56) References Cited

U.S. PATENT DOCUMENTS

| | | | | |
|---|---|---|---|---|
| 2009/0099582 | A1 | 4/2009 | Isaacs et al. | |
| 2009/0099583 | A1 | 4/2009 | Butterfield et al. | |
| 2009/0216228 | A1 | 8/2009 | Masuda | |
| 2009/0270891 | A1* | 10/2009 | Beaupre | A61B 17/32009 606/169 |
| 2013/0218185 | A1* | 8/2013 | Sanai | A61B 17/32009 606/169 |

OTHER PUBLICATIONS

Dec. 8, 2015 International Preliminary Report on Patentability issued in International Patent Application No. PCT/JP2014/065132.

* cited by examiner

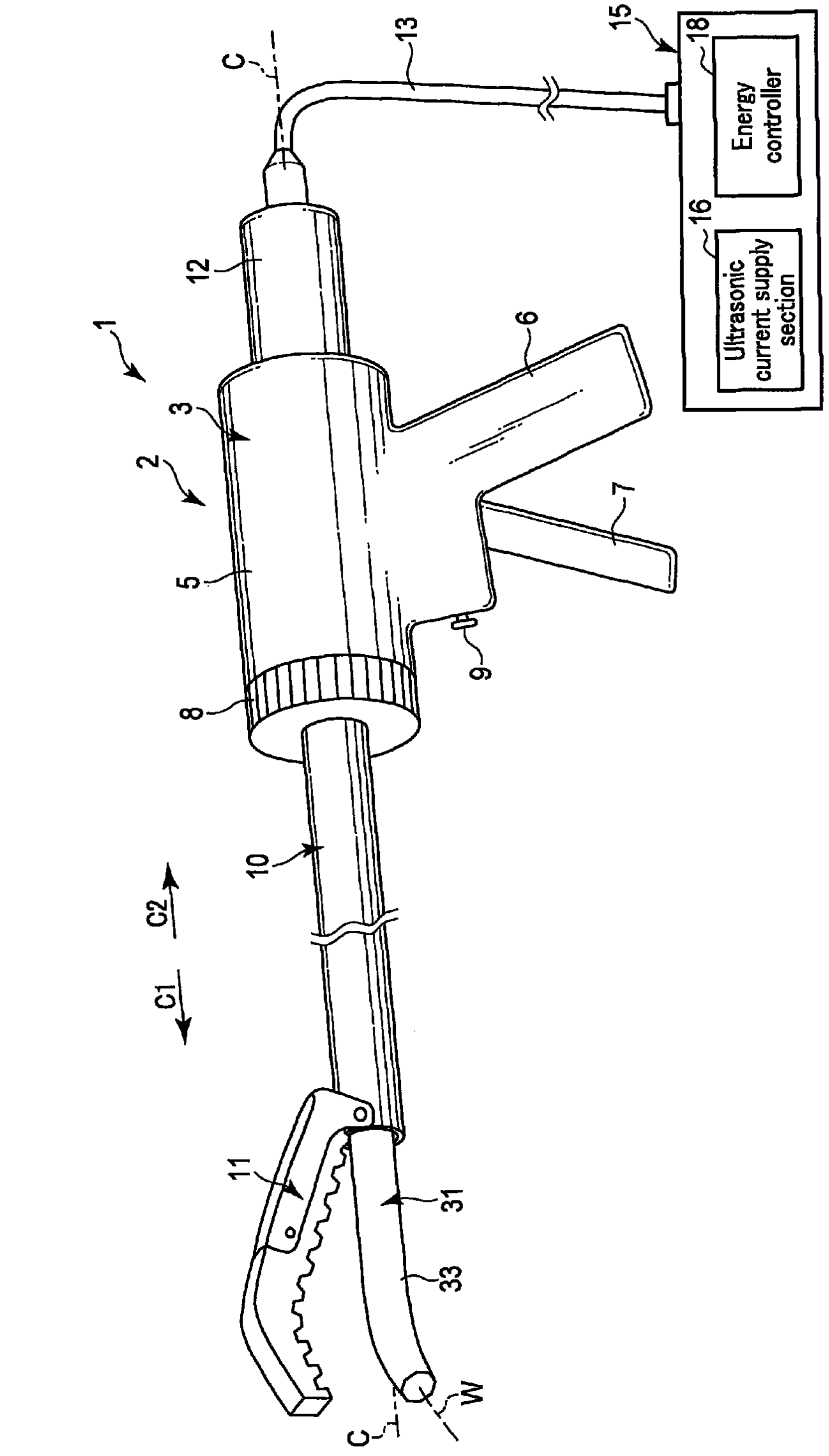
F I G. 1

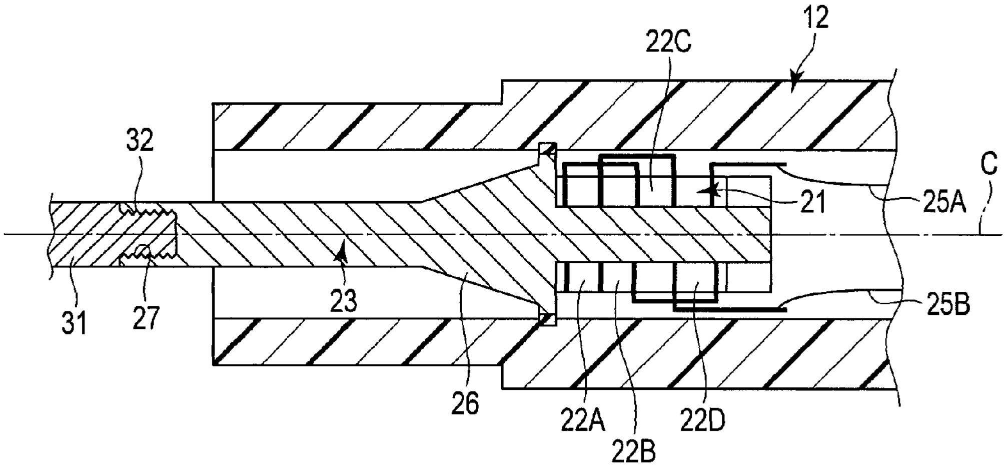
F I G. 2
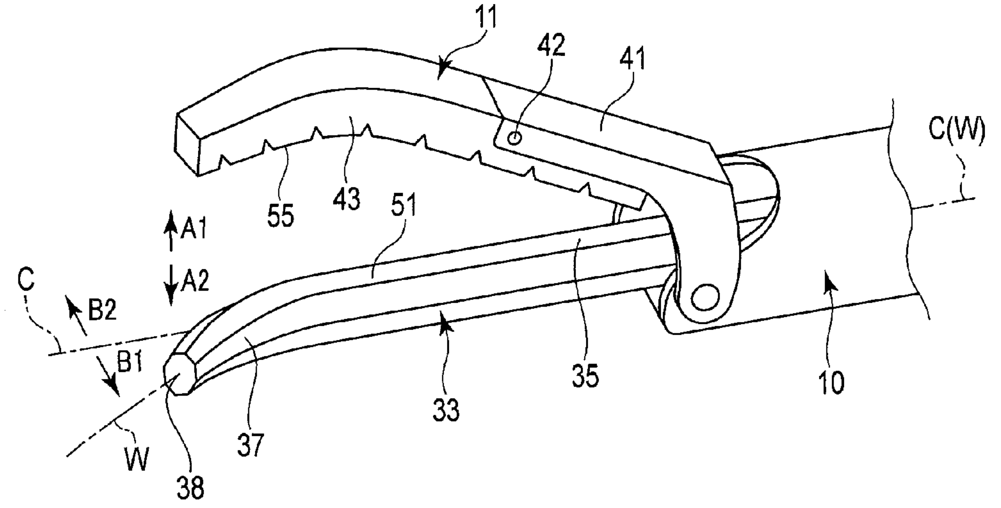
F I G. 3

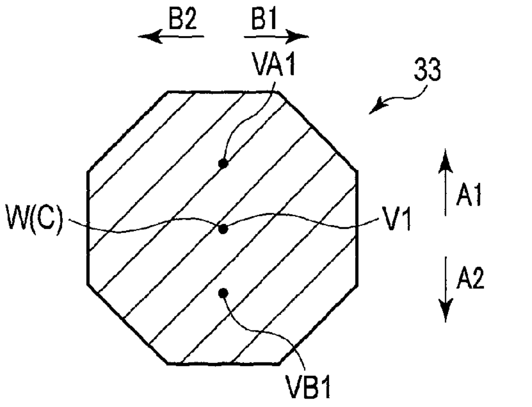
F I G. 8
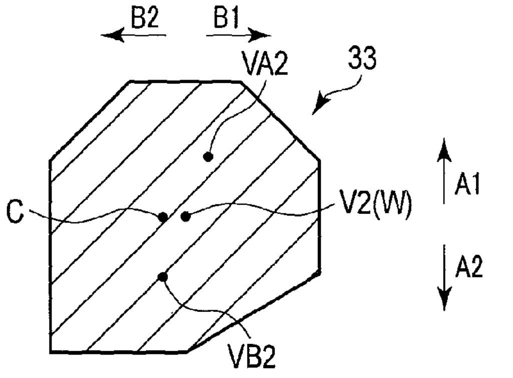
F I G. 9
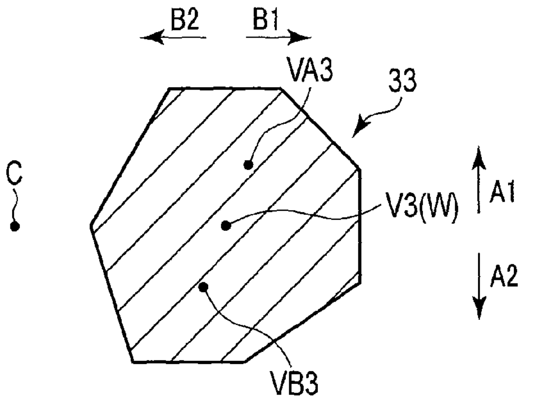
F I G. 10

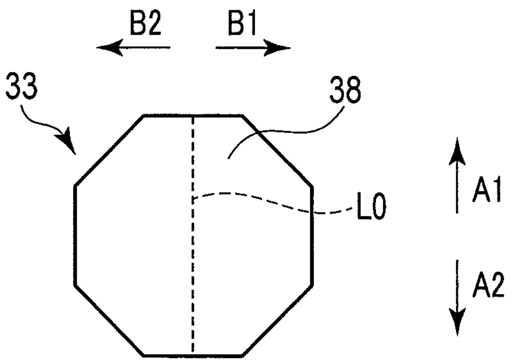
F I G. 11
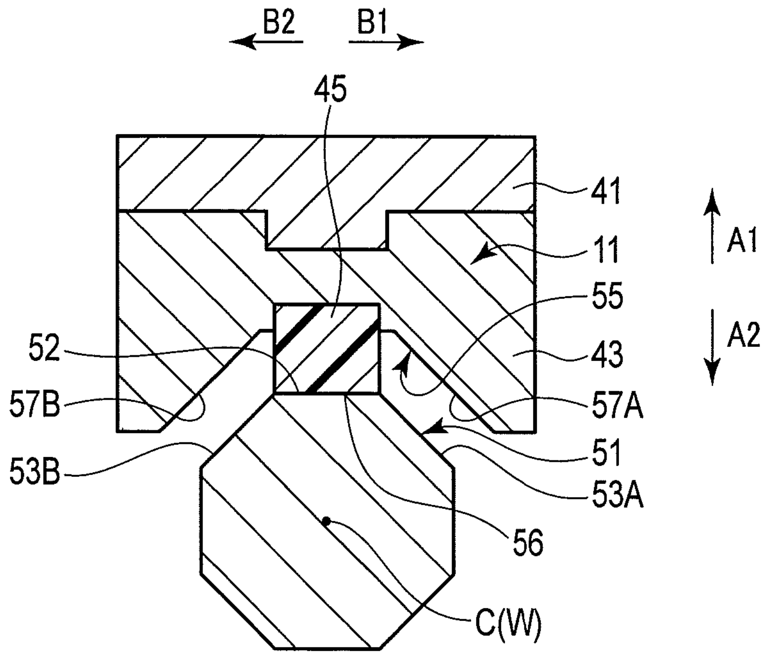
F I G. 12

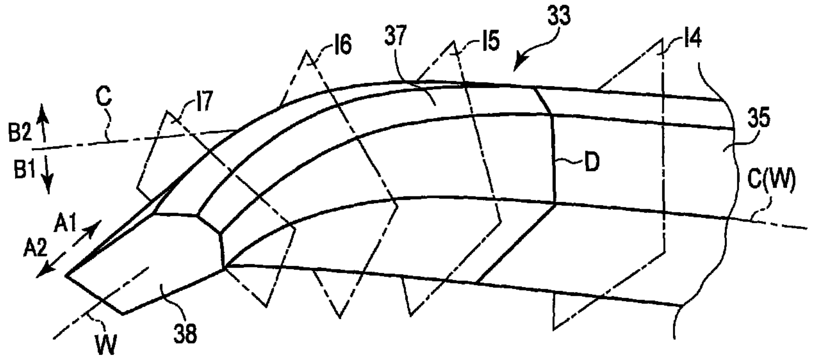
F I G. 15
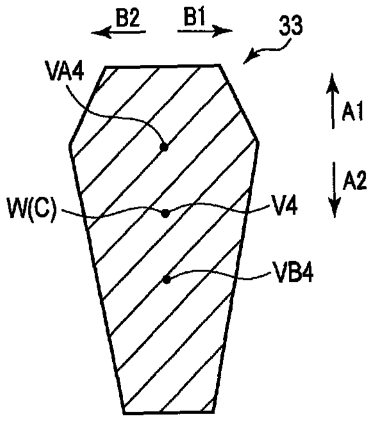
F I G. 16

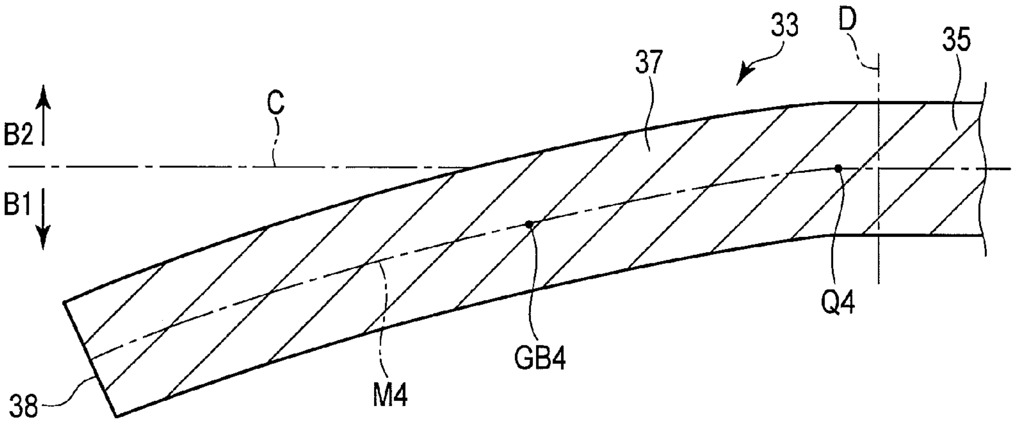
F I G. 20
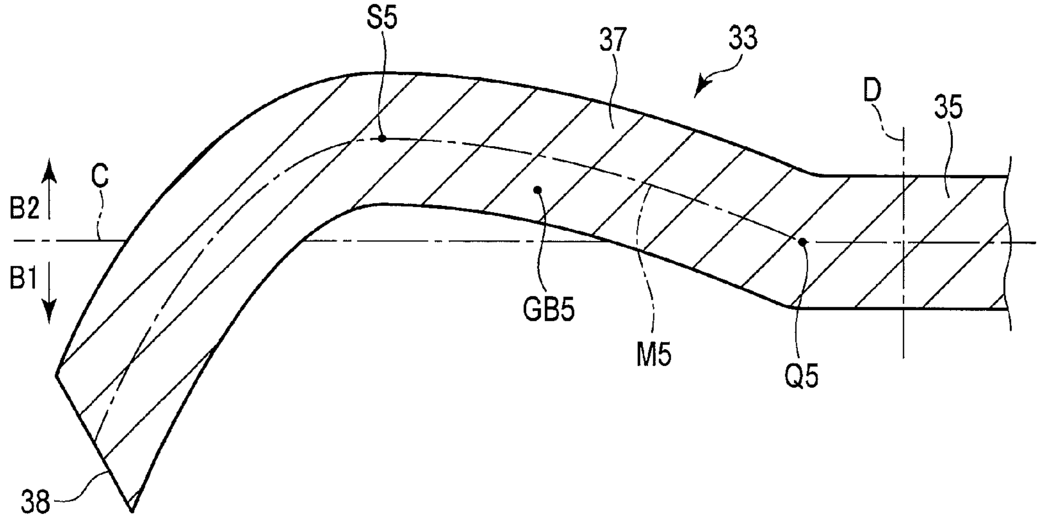
F I G. 21

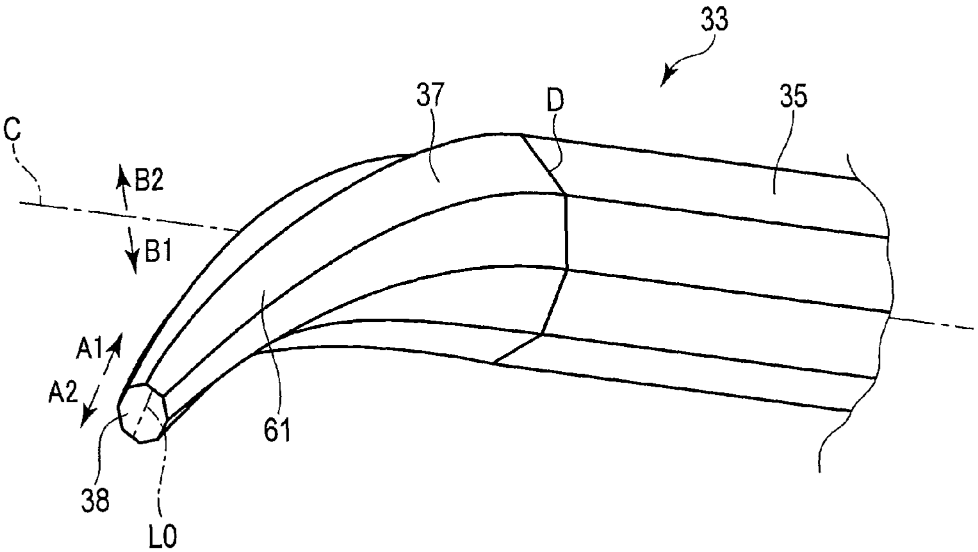
F I G. 22
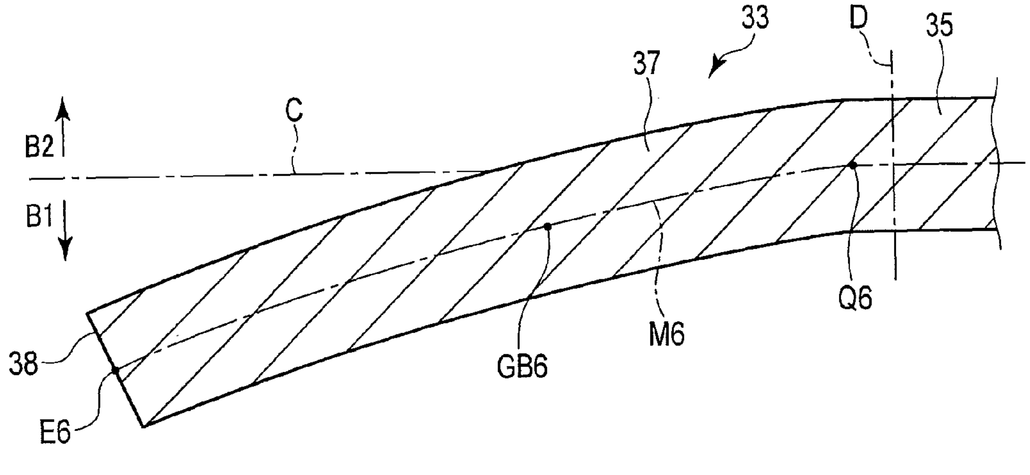
F I G. 23

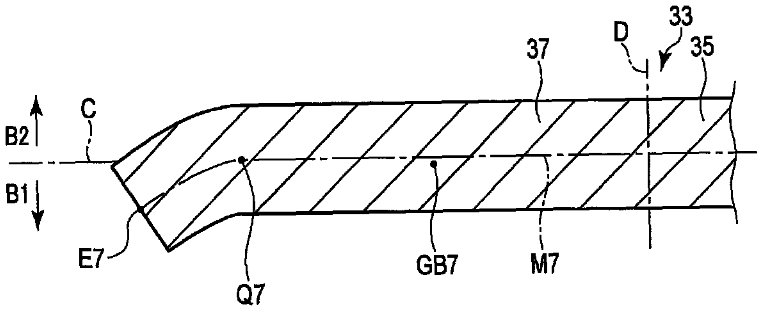
F I G. 24
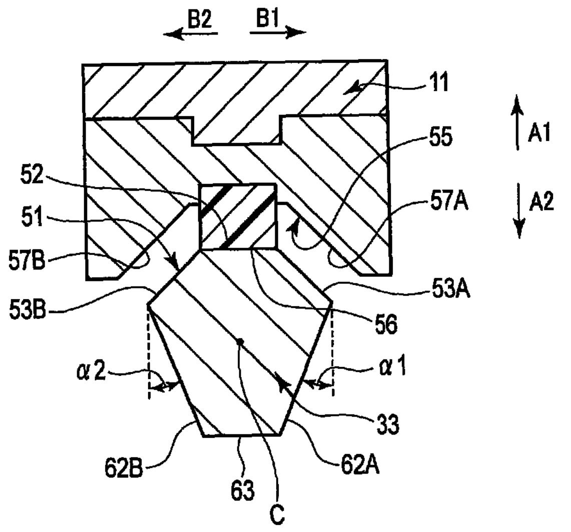
F I G. 25

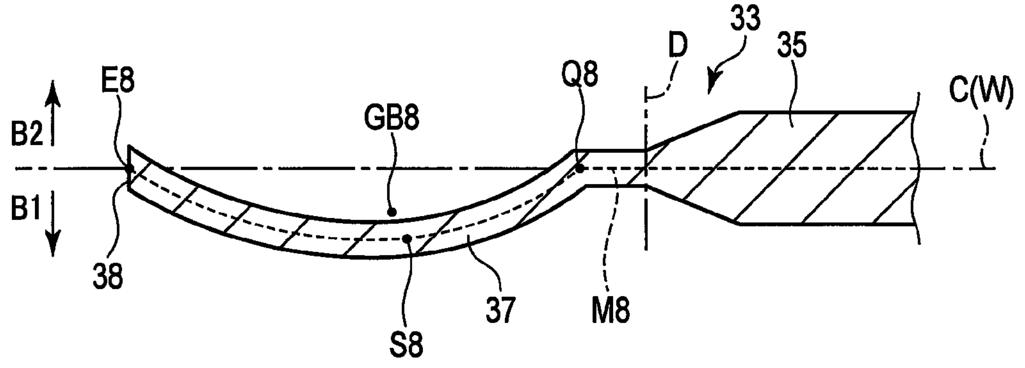
F I G. 27
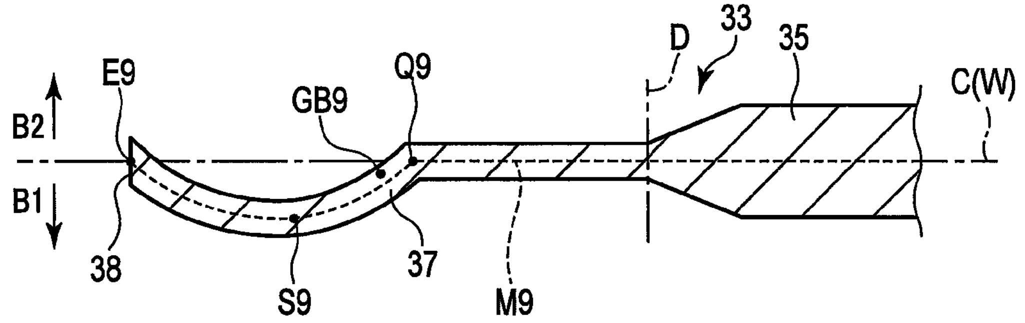
F I G. 28

ULTRASONIC PROBE AND ULTRASONIC TREATMENT APPARATUS

CROSS-REFERENCE TO RELATED APPLICATIONS

This is a Continuation Application of PCT Application No. PCT/JP2014/065132, filed Jun. 6, 2014 and based upon and claiming the benefit of priority from prior Japanese Patent Application No. 2013-121019, filed Jun. 7, 2013, the entire contents of which are incorporated herein by reference.

BACKGROUND OF THE INVENTION

1. Field of the Invention

The present invention relates to an ultrasonic probe which transmits an ultrasonic vibration, and an ultrasonic treatment apparatus including the ultrasonic probe.

2. Description of the Related Art

U.S. Patent Application Publication No. 2009/0099583 discloses an ultrasonic treatment apparatus including an ultrasonic probe configured to transmit an ultrasonic vibration from a proximal direction toward a distal direction. In this ultrasonic treatment apparatus, a distal treatment section is provided in a distal portion of the ultrasonic probe. In addition, a jaw, which is openable and closable relative to the distal treatment section, is provided. The ultrasonic probe includes a probe main body portion which is provided to extend along a longitudinal axis with the longitudinal axis being an axial center, and a probe bend portion which is provided on the distal direction side with respect to the probe main body portion. The probe bend portion is located in the distal treatment section, and bends relative to the probe main body portion in a bend direction which is one side of a direction perpendicular to the longitudinal axis and perpendicular to the opening or closing direction of the jaw. With the provision of the probe bend portion, the visibility of a surgeon is secured in a state in which a treatment target such as a living body tissue is grasped between the jaw and the distal treatment section, and it becomes easier for the surgeon to make the distal treatment section reach a position where the treatment target can be grasped. Specifically, with the provision of the probe bend portion, it becomes easier for the surgeon to use the ultrasonic probe in the treatment.

BRIEF SUMMARY OF THE INVENTION

According to one aspect of the invention, an ultrasonic probe includes that: a probe main body portion which extends along the longitudinal axis with the longitudinal axis being an axial center, and which is configured to transmit an ultrasonic vibration along the longitudinal axis from a proximal direction toward a distal direction; and a probe bend portion which is provided on the distal direction side with respect to the probe main body portion, when one direction perpendicular to the longitudinal axis is set to be a first bend direction and an opposite side to the first bend direction is set to be a second bend direction, the probe bend portion bending relative to the probe main body portion in the first bend direction and the second bend direction in a state in which a center of gravity is located on a first bend direction side with respect to the longitudinal axis, the probe bend portion being configured such that, when one side of a direction, which is perpendicular to the longitudinal axis and is perpendicular to the first bend direction and the second bend direction, is set to be a first perpendicular direction and an opposite side to the first perpendicular direction is set to be a second perpendicular direction, a cross-sectional shape of the probe bend portion in a cross section perpendicular to the first perpendicular direction and the second perpendicular direction varies continuously along the first perpendicular direction and second perpendicular direction in a state in which a cross-sectional center of gravity of the probe bend portion in the cross section perpendicular to the first perpendicular direction and the second perpendicular direction lies toward the second bend direction side, as it is from the first perpendicular direction toward the second perpendicular direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view illustrating a structure of an ultrasonic treatment apparatus according to a first embodiment.

FIG. 2 is a cross-sectional view which schematically illustrates an internal structure of a vibrator case according to the first embodiment.

FIG. 3 is a perspective view which schematically illustrates structures of a distal portion of an ultrasonic probe, a distal portion of a sheath and a jaw according to the first embodiment.

FIG. 8 is a cross-sectional view illustrating a cross section I1 in FIG. 4.

FIG. 9 is a cross-sectional view illustrating a cross section I2 in FIG. 4.

FIG. 10 is a cross-sectional view illustrating a cross section I3 in FIG. 4.

FIG. 11 is a schematic view illustrating a distal surface of the ultrasonic probe according to the first embodiment.

FIG. 12 is a cross-sectional view which schematically illustrates the jaw and distal treatment section according to the first embodiment by a cross section perpendicular to the longitudinal axis.

FIG. 15 is a perspective view which schematically illustrates a structure of a distal treatment section of an ultrasonic probe according to a first modification of the first embodiment.

FIG. 16 is a cross-sectional view illustrating a cross section I4 in FIG. 15.

FIG. 20 is a cross-sectional view which schematically illustrates a distal treatment section according to a second modification of the first embodiment by a cross section which is perpendicular to the first perpendicular direction and the second perpendicular direction and is on the first perpendicular direction side with respect to the longitudinal axis.

FIG. 21 is a cross-sectional view which schematically illustrates the distal treatment section according to the second modification by a cross section which is perpendicular to the first perpendicular direction and the second perpendicular direction and is on the second perpendicular direction side with respect to the longitudinal axis.

FIG. 22 is a perspective view which schematically illustrates a structure of a distal treatment section of an ultrasonic probe according to a third modification of the first embodiment.

FIG. 23 is a cross-sectional view which schematically illustrates the distal treatment section according to the third modification by a cross section which is perpendicular to the first perpendicular direction and the second perpendicular direction and is on the first perpendicular direction side with respect to the longitudinal axis.

FIG. 24 is a cross-sectional view which schematically illustrates the distal treatment section according to the third modification by a cross section which is perpendicular to the first perpendicular direction and the second perpendicular direction and is on the second perpendicular direction side with respect to the longitudinal axis.

FIG. 25 is a cross-sectional view which schematically illustrates a jaw and a distal treatment section according to a fourth modification of the first embodiment by a cross section which is perpendicular to the longitudinal axis.

FIG. 27 is a cross-sectional view which schematically illustrates a distal treatment section according to the second embodiment by a cross section which is perpendicular to the first perpendicular direction and the second perpendicular direction and is on the first perpendicular direction side with respect to the longitudinal axis.

FIG. 28 is a cross-sectional view which schematically illustrates the distal treatment section according to the second embodiment by a cross section which is perpendicular to the first perpendicular direction and the second perpendicular direction and is on the second perpendicular direction side with respect to the longitudinal axis.

DETAILED DESCRIPTION OF THE INVENTION

First Embodiment

Figure 4:
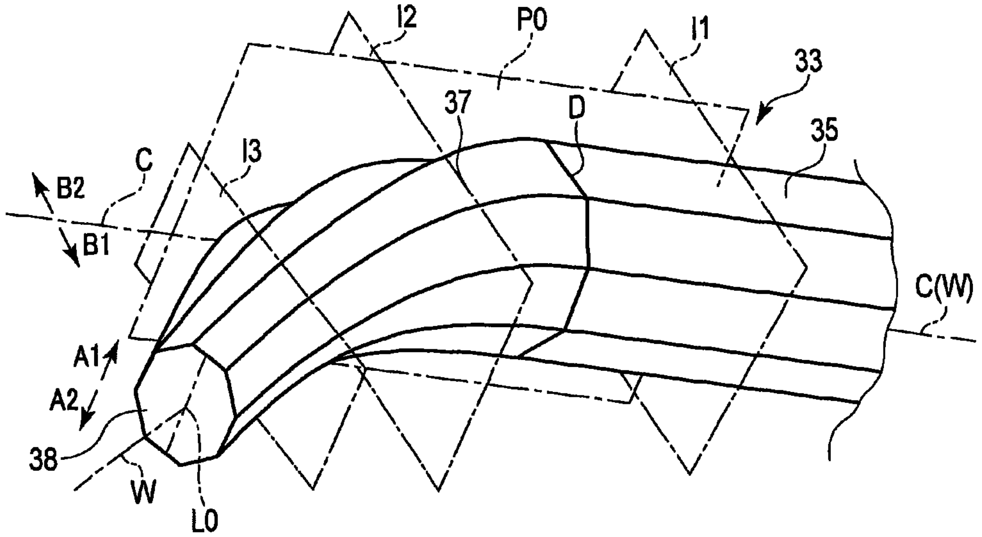
FIG. 4 is a perspective view which schematically illustrates a structure of a distal treatment section of the ultrasonic probe according to the first embodiment.

A first embodiment of the present invention is described with reference to FIG. 1 to FIG. 14.

FIG. 1 is a view illustrating a structure of an ultrasonic treatment apparatus 1 of the present embodiment. As illustrated in FIG. 1, the ultrasonic treatment apparatus 1 has a longitudinal axis C. Here, one side of direction parallel to the longitudinal axis C is a distal direction (direction of arrow C1 in FIG. 1), and direction opposite to the distal direction is a proximal direction (direction of arrow C2 in FIG. 1). In addition, each of the distal direction and the proximal direction is a longitudinal axis direction which is parallel to the longitudinal axis C. The longitudinal axis C is an axis extending in a straight line. In the present embodiment, the ultrasonic treatment device 1 is an ultrasonic coagulation-and-cutting treatment apparatus which performs coagulation and cutting of a living body tissue, etc., by using an ultrasonic vibration.

The ultrasonic treatment apparatus 1 includes a holding unit 3. The holding unit 3 includes a cylindrical case portion 5 which is provided to extend along the longitudinal axis C, a stationary handle 6 which is formed integral with the cylindrical case portion 5, and a movable handle 7 which is pivotably attached to the cylindrical case portion 5. The movable handle 7 pivots about a position of attachment to the cylindrical case portion 5, and thereby the movable handle 7 performs an opening motion or a closing motion relative to the stationary handle 6. In addition, the holding unit 3 includes a rotary operation knob 8 which is attached on the distal direction side of the cylindrical case portion 5. The rotary operation knob 8 is rotatable about the longitudinal axis C relative to the cylindrical case portion 5. Besides, an energy operation input button 9, which is an energy operation input section, is attached to the stationary handle 6.

The ultrasonic treatment apparatus 1 includes a sheath 10 which is provided to extend along the longitudinal axis C. The sheath 10 is inserted in an inside of the rotary operation knob 8 and an inside of the cylindrical case portion 5 from the distal direction side, and thereby the sheath 10 is attached to the holding unit 3. A jaw 11 is pivotably attached to a distal portion of the sheath 10. The movable handle 7 is connected to a movable cylindrical portion (not shown) of the sheath 10 in the inside of the cylindrical case portion 5. A distal end of the movable cylindrical portion is connected to the jaw 11. The movable cylindrical portion moves along the longitudinal axis C by opening or closing the movable handle 7 relative to the stationary handle 6. Thereby, the jaw 11 pivots about a position of attachment to the sheath 10. In addition, the sheath 10 and jaw 11 are rotatable integral with the rotary operation knob 8, about the longitudinal axis C relative to the cylindrical case portion 5.

In addition, the ultrasonic treatment device 1 includes a vibrator case 12 which is provided to extend along the longitudinal axis C. The oscillator case 12 is inserted in the inside of the cylindrical case portion 5 from the proximal direction side, and thereby the vibrator case 12 is attached to the holding unit 3. In the inside of the cylindrical case portion 5, the transducer case 12 is coupled to the sheath 10. The vibrator case 12 is rotatable integral with the rotary operation knob 8, about the longitudinal axis C relative to the cylindrical case portion 5. In addition, one end of a cable 13 is connected to the oscillator case 12. The other end of the cable 13 is connected to a control unit 15. The control unit 15 includes an ultrasonic current supply section 16 and an energy controller 18. Here, the control unit 15 is an energy generator including, for example, a CPU (Central Processing Unit), an ASIC (Application Specification Integrated Circuit), etc. Besides, the ultrasonic current supply section 16 is an electric power supply which is provided, for example, in the energy generator, and the energy controller 18 is constituted by an electronic circuit (control circuit) which is provided, for example, in a CPU, ASIC, etc.

FIG. 2 is a view illustrating an internal structure of the vibrator case 12. As illustrated in FIG. 2, in an inside of the transducer case 12, there is provided an ultrasonic vibrator 21 which is an ultrasonic generation section configured to generate an ultrasonic vibration by being supplied with a current. The ultrasonic oscillator 21 includes a plurality of (four in this embodiment) piezoelectric elements 22A to 22D configured to convert an electric current to a vibration. The ultrasonic vibrator 21 is mounted on a horn member 23 which is provided to extend along the longitudinal axis C. An ultrasonic vibration, which occurs in the ultrasonic vibrator 21, is transmitted to the horn member 23. A cross-sectional area varying portion 26 is formed in the horn member 23. In the cross-sectional area varying portion 26, the cross-sectional area perpendicular to the longitudinal axis C decreases toward the distal direction. Thus, the amplitude of the ultrasonic vibration is increased in the cross-sectional area varying portion 26. A female screw portion 27 is provided in a distal portion of the horn member 23.

A columnar ultrasonic probe 31 is provided to extend on the distal direction side of the horn member 23. A male screw portion 32 is provided in a proximal portion of the ultrasonic probe 31. The male screw portion 32 is engaged with the female screw portion 27, and thereby the ultrasonic probe 31 is connected to the distal direction side of the horn member 23. The horn member 23 is provided to extend up to the inside of the cylindrical case portion 5, and the ultrasonic probe 31 is connected to the horn member 23 in the inside of the cylindrical case portion 5. The ultrasonic probe 31 extends from the inside of the cylindrical case portion 5 through the inside of the rotary operation knob 8 and an inside of the sheath 10. In addition, as illustrated in FIG. 1, the ultrasonic probe 31 is inserted through the sheath 10 in the state in which the ultrasonic probe 31 projects from a distal end of the sheath 10 toward the distal direction. Incidentally, the ultrasonic vibrator 21, horn member 23 and ultrasonic probe 31 are rotatable integral with the rotary operation knob 8, about the longitudinal axis C relative to the cylindrical case portion 5.

One end of each of electric wiring lines 25A, 25B is connected to the ultrasonic transducer 21. The electric wiring lines 25A, 25B extend through an inside of the cable 13, and the other ends thereof are connected to the ultrasonic current supply section 16 of the control unit 15. An ultrasonic generation current is supplied from the ultrasonic current supply section 16 to the ultrasonic vibrator 21 via the electric wiring lines 25A, 25B, and thereby the ultrasonic vibration occurs in the ultrasonic oscillator 21. Then, the generated ultrasonic vibration is transmitted to the ultrasonic probe 31 via the horn member 23. In addition, in the ultrasonic probe 31, the ultrasonic vibration is transmitted from the proximal direction toward the distal direction. Here, the proximal end of the ultrasonic vibrator 21 and the distal end of the ultrasonic probe 3 are at antinode positions of the ultrasonic vibration. In addition, the ultrasonic vibration is transmitted to the ultrasonic probe 31, and thereby the ultrasonic probe 31 performs such longitudinal vibration that the vibration direction and the transmission direction of a vibration are parallel to the longitudinal axis C.

The energy controller 18 is configured to control, based on an input of an energy operation in the energy operation input button 9, a supply state of an ultrasonic generation current from the ultrasonic current supply section 16. A switch (not shown) is provided in the inside of the stationary handle 6. The switch is closed by the pressing of the energy operation input button 9 and the input of the energy operation. The switch is electrically connected to the energy controller 18. By the switch being closed, an electric signal is transmitted to the energy controller 18, and the input of the energy operation is detected. By the input of the energy operation being detected, an ultrasonic generation current is supplied from the ultrasonic current supply section 16 to the ultrasonic transducer 21, the ultrasonic vibration occurs in the ultrasonic vibrator 21.

FIG. 3 is a view illustrating structures of a distal portion of the ultrasonic probe 31, a distal portion of the sheath 10 and the jaw 11. As illustrated in FIG. 3, the ultrasonic probe 31 includes a distal treatment section 33 which projects from the distal end of the sheath 10 toward the distal direction. At the distal treatment section 33, a treatment target such as a living tissue is treated by using the ultrasonic vibration which is transmitted. The jaw 11 turns relative to the sheath 10, and thereby the jaw 11 performs an opening motion or a closing motion relative to the distal treatment section 33. Here, one side of direction, which is perpendicular to the longitudinal axis C, is a jaw opening direction (direction of arrow A1 in FIG. 3), and the opposite side to the jaw opening direction is a jaw closing direction (direction of arrow A2 in FIG. 3).

FIG. 4 is a view illustrating a structure of the distal treatment section 33 of the ultrasonic probe 31. As illustrated in FIG. 3 and FIG. 4, the ultrasonic probe 31 is provided to extend along a center-of-gravity axis W. In addition, the ultrasonic probe 31 includes a probe main body portion 35 which extends along the longitudinal axis C with the longitudinal axis C being an axial center. In a cross section perpendicular to the center-of-gravity axis W, a position where the center-of-gravity axis W passes becomes a transverse cross-sectional center of gravity (perpendicular-to-axis cross-sectional center of gravity) V of the cross section. In the probe main body 35, the center-of-gravity axis W is coaxial with the longitudinal axis C. Here, a symmetry reference plane P0, which passes through the longitudinal axis C and is perpendicular to the jaw opening direction and the jaw closing direction, is defined. The probe main body portion 35 is formed in plane symmetry with the symmetry reference plane P0 being as a central plane. In addition, a center of gravity GA (not shown in the Figure) of the probe main body portion 35 is located on the longitudinal axis C. In the probe main body portion 35, the ultrasonic vibration is transmitted along the longitudinal axis C from the proximal direction toward the distal direction.

In addition, one direction, which is different from the jaw opening direction (direction of arrow A1 in FIG. 3 and FIG. 4) and jaw closing direction (direction of A2 in FIG. 3 and FIG. 4) and is perpendicular to the longitudinal axis C, is set to be a first bend direction (direction of arrow B1 in FIG. 3 and FIG. 4), and the opposite side to the first bend direction is set to be a second bend direction (direction of arrow B2 in FIG. 3 and FIG. 4). Here, the jaw opening direction corresponds to a first perpendicular direction which is one side of a direction which is perpendicular to the longitudinal axis C and is perpendicular to the first bend direction and the second bed direction. In addition, the jaw closing direction corresponds to a second perpendicular direction which is the other side of the direction which is perpendicular to the longitudinal axis C and is perpendicular to the first bend direction and the second bed direction.

The ultrasonic probe 31 is provided with a probe bend portion 37 located on the distal direction side with respect to the probe main body portion 35. In this embodiment, the probe bend portion 37 is a part of the distal treatment section 33 and is located in the distal treatment section 33. The probe bend portion 37 is continuous on the distal direction side of the probe main body portion 35, and bends toward the first bend direction. Specifically, the probe bend portion 37 bends in the first bend direction and second bend direction, relative to the probe main body portion 35. The probe bend portion 37 is formed in plane asymmetry with the symmetry reference plane P0 being as a central plane. In addition, the center of gravity GB of the probe bend portion 37 is located on the first bend direction side with respect to the longitudinal axis C. Incidentally, in the probe bend portion 37, the center-of-gravity axis W bends toward the first bend direction relative to the longitudinal axis C.

Figure 5:
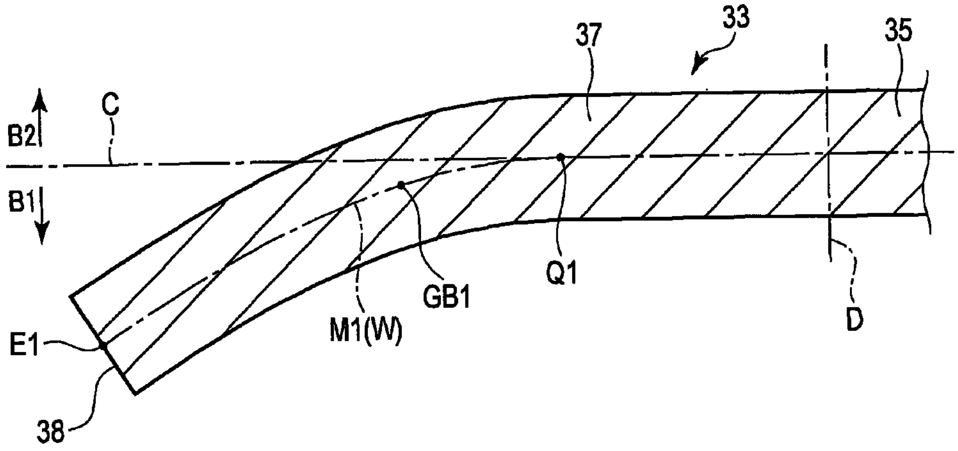
FIG. 5 is a cross-sectional view which schematically illustrates the distal treatment section according to the first embodiment by a cross section which is perpendicular to a first perpendicular direction and a second perpendicular direction and passes through a longitudinal axis.
Figure 6:
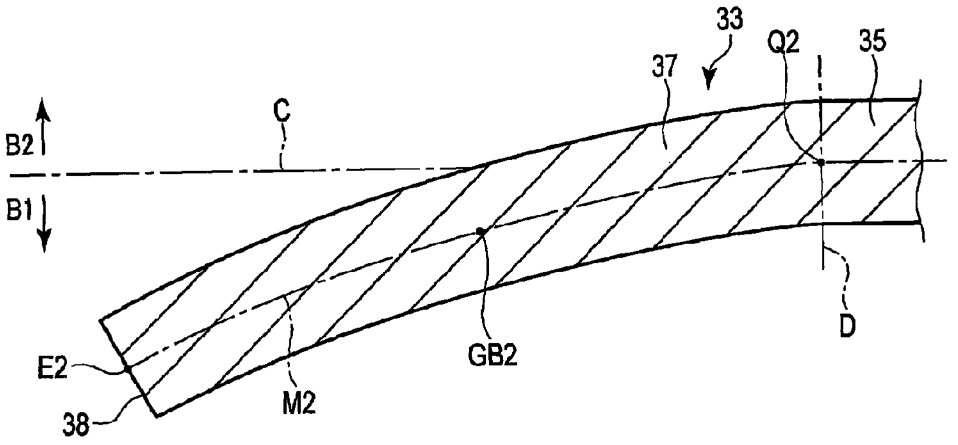
FIG. 6 is a cross-sectional view which schematically illustrates the distal treatment section according to the first embodiment by a cross section which is perpendicular to the first perpendicular direction and the second perpendicular direction and is on the first perpendicular direction side with respect to the longitudinal axis.
Figure 7:
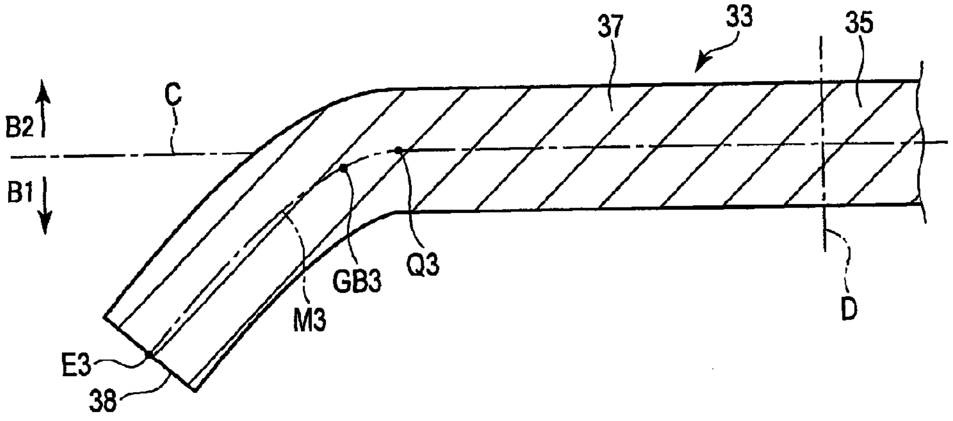
FIG. 7 is a cross-sectional view which schematically illustrates the distal treatment section according to the first embodiment by a cross section which is perpendicular to the first perpendicular direction and the second perpendicular direction and is on the second perpendicular direction side with respect to the longitudinal axis.

FIG. 5 to FIG. 7 are views illustrating the distal treatment section 33 by cross sections perpendicular to the first perpendicular direction and second perpendicular direction. Here, FIG. 5 is a cross section passing through the longitudinal axis C. In addition, FIG. 6 is a cross section on the first perpendicular direction side (jaw opening direction side) with respect to the cross section of FIG. 5. FIG. 7 is a cross section on the second perpendicular direction side (jaw closing direction side) with respect to the cross section of FIG. 5.

As illustrated in FIG. 5 to FIG. 7, in each of the cross sections perpendicular to the first perpendicular direction and the second perpendicular direction of the distal treatment section 33, a cross-sectional center axis (a corresponding one of M1~M3), which passes through the center position of the ultrasonic probe 31 in the first bend direction (direction of arrow B1 in FIG. 5 to FIG. 7) and the second bend direction (direction of arrow B2 in FIG. 5 to FIG. 7), is defined. In the probe main body portion 35, each of the cross-sectional center axes (M1~M3) extends parallel to the longitudinal axis C, and extends onto the symmetry reference plane P0.

In addition, in each of the cross sections perpendicular to the first perpendicular direction and the second perpendicular direction, an axis bend proximal end (a corresponding one of Q1~Q3), at which the extending direction of the cross-sectional center axis (a corresponding one of M1~M3) becomes nonparallel to the longitudinal axis C, is located on the probe bend portion 37. On each of the cross-sectional center axes (M1~M3), the axis bend proximal end (a corresponding one of Q1~Q3) becomes a bend start position at which the bending relative to the longitudinal axis C begins. On the distal direction side with respect to each of the axis bend proximal ends (Q1~Q3), the cross-sectional center axis (a corresponding one of M1~M3) bends toward the first bend direction, and is provided to extend in a state of being away from the symmetry reference plane P0 in a first bending direction. The position in the axis bend proximal ends (Q1~Q3) in the longitudinal axis direction parallel to the longitudinal axis C varies along the first perpendicular direction and the second perpendicular direction. Specifically, the position in the axis bend proximal ends (Q1~Q3) is toward the distal direction side, as the position therein is from the first perpendicular direction (jaw opening direction) toward the second perpendicular direction (jaw closing direction). Accordingly, the axis bend proximal end (bend start position) Q1 in the cross section of FIG. 5 is located on the distal direction side with respect to the axis bend proximal end (bend start position) Q2 in the cross section of FIG. 6, and is located on the proximal direction side with respect to the axis bend proximal end (bend start position) Q3 in the cross section of FIG. 7. Incidentally, the cross-sectional center axis M1 in the cross section of FIG. 5, which passes through the longitudinal axis C, coincides with the center-of-gravity axis W of the ultrasonic probe 31.

In each of the cross sections perpendicular to the first perpendicular direction and the second perpendicular direction, in a part on the distal direction side with respect to the axis bend proximal end (a corresponding one of Q1~Q3), the cross-sectional center axis (a corresponding one of M1~M3) bends with a curvature (a corresponding one of R1~R3). The curvatures (R1~R3) in the cross-sectional center axes (M1~M3) vary along the first perpendicular direction and the second perpendicular direction. Specifically, the curvatures (R1~R3) in the cross-sectional center axes (M1~M3) become greater, as a position therein is from the first perpendicular direction (jaw opening direction) toward the second perpendicular direction (jaw closing direction). Accordingly, the curvature R1 of the cross-sectional center axis M1 in the cross section of FIG. 5 is greater than the curvature R2 of the cross-sectional center axis M2 in the cross section of FIG. 6, and is less than the curvature R3 of the cross-sectional center axis M3 in the cross section of FIG. 7.

In each of the cross sections perpendicular to the first perpendicular direction and the second perpendicular direction, in a part on the proximal direction side with respect to the axis bend proximal end (a corresponding one of Q1~Q3) of the probe bend portion 37, the cross-sectional center axis (a corresponding one of M1~M3) is provided to extend in parallel to the longitudinal axis C, like the probe main body portion 35. Here, among the cross sections perpendicular to the first perpendicular direction and the second perpendicular direction, the cross section, in which the axis bend proximal end is located most proximally, is set to be a boundary-defining cross section. In the present embodiment, the position in the axis bend proximal ends (Q1~Q3) is toward the distal direction side, as the position therein is from the first perpendicular direction toward the second perpendicular direction. Thus, a cross section (contact surface) passing through a first-perpendicular-direction-side end of the probe bend portion 37 becomes a boundary-defining cross section. For example, the cross section of FIG. 6, which is located on the first perpendicular direction side with respect to the cross section of FIG. 5, is set to be the boundary-defining cross section passing through the first-perpendicular-direction-side end of the probe bend portion 37. In this case, the boundary D between the probe main body portion 35 and the probe bend portion 37 in the longitudinal axis direction parallel to the longitudinal axis C coincides in position with the axis bend proximal end Q2 of the cross-sectional center axis M2. In other words, the boundary D between the probe main body portion 35 and the probe bend portion 37 in the longitudinal axis direction agrees with the axis bend proximal end of the cross-sectional center axis in the boundary-defining cross section. In the meantime, in the description of the present embodiment, the cross sections perpendicular to the first perpendicular direction and second perpendicular direction include a contact surface passing through the first-perpendicular-direction-side end of the probe bend portion 37 and a contact surface passing through a second-perpendicular-direction-side end of the probe bend portion 37. In addition, the center-of-gravity axis W of the ultrasonic probe 31 is coaxial with the longitudinal axis C in a part located on the proximal direction side with respect to the boundary D, and bends relative to the longitudinal axis C in a part located on the distal direction side with respect to the boundary D.

As described above, the cross-sectional shape of the probe bend portion 37 in the cross sections perpendicular to the first perpendicular direction and the second perpendicular direction varies continuously along the first perpendicular direction and the second perpendicular direction. Here, in each of the cross sections perpendicular to the first perpendicular direction and the second perpendicular direction, the cross-sectional center of gravity (GB1~GB3) of the probe bend portion 37 is defined. As described above, the cross-sectional shape of the probe bend portion 37 varies along the first perpendicular direction and the second perpendicular direction, and thereby the position of the cross-sectional center of gravity (GB1~GB3) of the probe bend portion 37 varies along the first perpendicular direction and the second perpendicular direction. Specifically, the cross-sectional center of gravity (GB1~GB3) of the probe bend portion 37 lies toward the second bend direction side, as it is from the first perpendicular direction (jaw opening direction) toward the second perpendicular direction (jaw closing direction). Accordingly, the cross-sectional center of gravity GB1 of the probe bend portion 37 in the cross section of FIG. 5 is located on the second bend direction side with respect to the cross-sectional center of gravity GB2 of the probe bend portion 37 in the cross section of FIG. 6, and is located on the first bend direction side with respect to the cross-sectional center of gravity GB3 of the probe bend portion 37 in the cross section of FIG. 7.

As described above, the position of the cross-sectional center of gravity (GB1~GB3) of the probe bend portion 37 shifts along the first perpendicular direction and second perpendicular direction, and thereby the distance of the center of gravity GB of the probe bend portion 37 from the longitudinal axis C toward the first bend direction becomes smaller. For example, even in the case where the distance of the cross-sectional center of gravity GB2 of the probe bend portion 37 from the longitudinal axis C toward the first bend direction becomes larger in the cross section of FIG. 6 passing through the first-perpendicular-direction-side part of the probe bend portion 37, the distance of the cross-sectional center of gravity GB3 of the probe bend portion 37 from the longitudinal axis C toward the first bend direction becomes smaller in the cross section of FIG. 7 passing through the second-perpendicular-direction-side part of the probe bend portion 37. The distance of the cross-sectional center of gravity of the probe bend portion 37 from the longitudinal axis C toward the first bend direction becomes smaller in the part on the second perpendicular direction side, and thereby the distance of the center of gravity GB of the probe bend portion 37 from the longitudinal axis C toward the first bend direction does not increase.

FIG. 8 to FIG. 10 are views illustrating the distal treatment section 33 by cross sections (transverse cross sections) perpendicular to the center-of-gravity axis W. FIG. 8 illustrates a cross section I1 in FIG. 4, FIG. 9 illustrates a cross section I2 in FIG. 4, and FIG. 10 illustrates a cross section I3 in FIG. 4. The cross-section I1 is a cross section on the proximal direction side with respect to the boundary D, and the cross section I2 and cross section I3 are cross sections on the distal direction side with respect to the boundary D. In addition, the cross section I3 is located on the distal direction side with respect to the cross section I2. Here, the center of gravity in the cross section perpendicular to the center-of-gravity axis W is set to be a transverse cross-sectional center of gravity (perpendicular-to-axis cross-sectional center of gravity) V. In addition, a half-part center of gravity on the first perpendicular direction side (direction side of arrow A1 in FIG. 8 to FIG. 10) with respect to the center-of-gravity axis W in the cross section perpendicular to the center-of-gravity axis W is set to be a first transverse cross-sectional half-part center of gravity VA, and a half-part center of gravity on the second perpendicular direction side (direction side of arrow A2 in FIG. 8 to FIG. 10) with respect to the center-of-gravity axis W in the cross section perpendicular to the center-of-gravity axis W is set to be a second transverse cross-sectional half-part center of gravity VB.

In the cross section I1 illustrated in FIG. 8, since the cross section I1 is located on the proximal direction side with respect to the boundary D, the center-of-gravity axis W is coaxial with the longitudinal axis C, and the longitudinal axis C passes through a lateral cross-sectional center of gravity V1. In addition, in the first bend direction (direction of arrow B1 in FIG. 8 to FIG. 10) and the second bend direction (direction of arrow B2 in FIG. 8 to FIG. 10), the first transverse cross-sectional half-part center of gravity VA1 and the second transverse cross-sectional half-part center of gravity VB1 are not displaced from the center-of-gravity axis W (transverse cross-sectional center of gravity V1).

In each of the cross section I2 illustrated in FIG. 9 and the cross section I3 illustrated in FIG. 10, since the cross section is located on the distal direction side with respect to the boundary D, the lateral cross-sectional center of gravity (a corresponding one of V2 and V3) is apart from the longitudinal axis C toward the first bend direction side. In addition, the distance from the longitudinal axis C to the transverse cross-sectional center of gravity V3 in the cross section I3 is greater than the distance from the longitudinal axis C to the transverse cross-sectional center of gravity V2 in the cross section I2. Besides, in each of the cross section I2 and cross section I3, the first transverse cross-sectional half-part center of gravity (a corresponding one of VA2 and VA3) is sifted toward the first bend direction side from the cross-sectional center of gravity (a corresponding one of V2 and V3), and the second transverse cross-sectional half-part center of gravity (a corresponding one of VB2 and VB3) is displaced toward the second bend direction side from the cross-sectional center of gravity (a corresponding one of V2 and V3). Thus, in the cross section I3, the distance in the first bend direction from the longitudinal axis C to the second lateral cross-sectional half-part center of gravity VB3 decreases, and, in the cross section 12, the second transverse cross-sectional half-part center of gravity VB2 does not deviate from the longitudinal axis C in the first bend direction and the second bend direction.

As described above, in the probe bend portion 37, the distance of the second transverse cross-sectional half-part center of gravity VB2, which is the half-part center of gravity on the second perpendicular direction side with respect to the transverse cross-sectional center of gravity V, from the longitudinal axis C toward the first bend direction becomes smaller or zero. Thereby, the distance of the center of gravity GB of the probe bend portion 37 from the longitudinal axis C toward the first bend direction is not large.

The probe bend portion 37 includes a distal surface 38 which forms a distal end of the ultrasonic probe 31. FIG. 11 is a view illustrating the distal surface 38 of the probe bend portion 37. As illustrated in FIG. 11, on the distal surface 38, a distal surface center line L0 is defined, which passes through a center position of the ultrasonic probe 31 in the first bend direction (direction of arrow B1 in FIG. 11) and the second bend direction (direction of arrow B2 in FIG. 11). The distal surface center line L0 is parallel to the first perpendicular direction (direction of arrow A1 in FIG. 11) and the second perpendicular direction (direction of arrow A2 in FIG. 11).

As illustrated in FIG. 5 to FIG. 7, the distal end (E1~E3) of each of the cross-sectional center axes (M1~M3) is located on the distal surface 38. Specifically, in each of the cross sections perpendicular to the first perpendicular direction and the second perpendicular direction, the cross-sectional center axis (a corresponding one of M1~M3) extends to the distal surface 38. Accordingly, the dimension of the probe bend portion 37 in the first perpendicular direction and the second perpendicular direction is constant over the entire length in the longitudinal axis direction that is parallel to the longitudinal axis C. The distal surface center line L0 is formed by making continuous the distal ends (E1~E3) of the cross-sectional center axes (M1~M3). Thus, the distal end of the cross-sectional center axis, which is defined in each of the cross sections perpendicular to the first perpendicular direction and the second perpendicular direction, coincides in position with the distal ends of the other cross-sectional center axes in the first bend direction and the second bend direction. Accordingly, in the first bend direction and second bend direction, the distal end E1 of the cross-sectional center axis M1 agrees in position with the distal end E2 of the cross-sectional center axis M2 and the distal end E3 of the cross-sectional center axis M3.

FIG. 12 is a view illustrating the distal treatment section 33 and jaw 11 by a cross section perpendicular to the longitudinal axis C. FIG. 12 illustrates a state in which the jaw 11 is closed relative to the distal treatment section 33. In addition, FIG. 12 is a cross section passing through a part on the proximal direction side with respect to the boundary D. As illustrated in FIG. 3 and FIG. 12, the jaw 11 includes a jaw body 41, a holding member 43 attached to the jaw body 41 via a connection pin 42, and a pad member 45 held by the holding member 43.

As illustrated in FIG. 12, the cross section of the distal treatment section 33 of the ultrasonic probe 31, which is perpendicular to the longitudinal axis C, is formed in a substantially octagonal shape. The distal treatment section 33 is provided with a probe-side facing-portion 51 which faces to the jaw 11 in the state in which the probe-side opposed-portion 51 faces in the first perpendicular direction (direction of arrow A1 in FIG. 12) that is the jaw opening direction. The probe-side facing-portion 51 includes a probe-side abutment surface 52 which is perpendicular to the first perpendicular direction and the second perpendicular direction (direction of arrow A2 in FIG. 12) in the state in which the pad member 45 abuts on the distal treatment section 33, and inclined facing-surfaces 53A and 53B which are inclined with respect to the probe-side abutment surface 52. The inclined opposed-surface (first inclined facing-surface) 53A is continuous with the first bend direction (direction of arrow B1 in FIG. 12) side of the probe-side abutment surface 52, and the inclined opposed-surface (second inclined counter-surface) 53B is continuous with the second bend direction (direction of arrow B2 in FIG. 12) side of the probe-side abutment surface 52.

Figure 13:
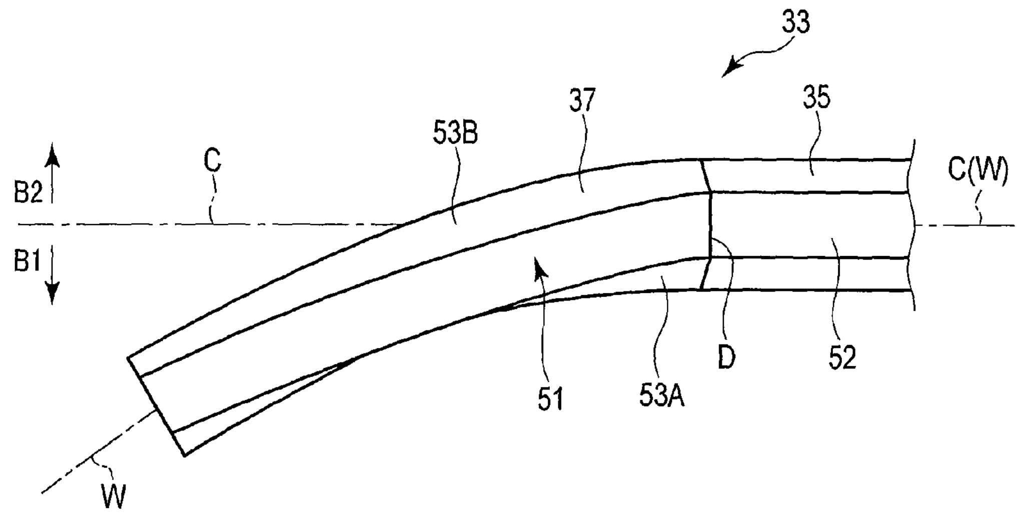
FIG. 13 is a schematic view illustrating a probe-side facing-portion of the distal treatment section according to the first embodiment, as viewed from the first perpendicular direction.

FIG. 13 is a view illustrating the probe-side facing-portion 51, as viewed from the first perpendicular direction (jaw opening direction). As illustrated in FIG. 13, the probe-side opposed-portion 51 bends toward the first bend direction (direction of arrow B1 in FIG. 13) relative to the longitudinal axis C in the probe bend portion 37. Specifically, the probe-side facing-portion 51 bends in the probe bend portion 37 in the first bend direction and the second bend direction (direction of arrow B2 in FIG. 13). Thereby, by the probe-side facing-portion 51, a first bend shape illustrated in FIG. 13 is formed.

As illustrated in FIG. 12, the jaw 11 is provided with a jaw-side facing-portion 55 which is opposed to the probe-side facing-portion 51, in a state in which the jaw-side opposed-portion 55 faces toward the second perpendicular direction (jaw closing direction). The jaw-side opposed-portion 55 includes a jaw-side abutment surface 56 which can abut on the probe-side abutment surface 52 of the probe-side facing-portion 51, in a state in which the jaw 11 is closed relative to the distal treatment section 33. Specifically, in the state in which the jaw 11 is closed relative to the distal treatment section 33, the jaw-side opposed-portion 55 can abut on the probe-side opposed-portion 51. The jaw-side abutment surface 56 is formed by the pad member 45. In addition, the jaw-side facing-portion 55 includes non-contact facing-surfaces 57A and 57B which do not come in contact with the probe-side facing-portion 51, in the state in which the jaw-side abutment surface 56 is in contact with the probe-side abutment surface 52. The non-contact opposed-surfaces 57A and 57B are formed by the holding member 43. The non-contact facing-surface (first non-contact facing-surface) 57A is located on the first bend direction side with respect to the jaw-side abutment surface 56, and the non-contact facing-surface (second non-contact facing-surface) 57B is located on the second bend direction side with respect to the jaw-side abutment surface 56.

Figure 14:
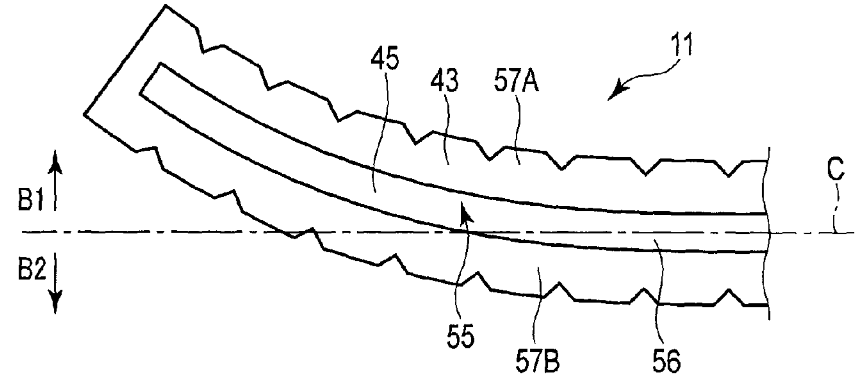
FIG. 14 is a schematic view illustrating a jaw-side facing-portion of the jaw according to the first embodiment, as viewed from the second perpendicular direction.

FIG. 14 is a view illustrating the jaw-side facing-portion 55, as viewed from the second perpendicular direction (jaw closing direction). As illustrated in FIG. 14, the jaw-side opposed-portion 55 bends toward the first bend direction (direction of arrow B1 in FIG. 14) relative to the longitudinal axis C, in accordance with the bending of the probe-side facing-portion 51. Specifically, the jaw-side facing-portion 55 bends in the first bend direction and the second bend direction (direction of arrow B2 in FIG. 14), in the state in which the jaw-side facing-portion 55 is opposed to the probe-side facing-portion 51. Thereby, by the jaw-side facing-portion 55, a second bend shape illustrated in FIG. 14, which corresponds to the first bend shape of the probe-side facing-portion 51, is formed. Since the jaw-side facing-portion 55 is formed in the second bend shape, which corresponds to the first bend shape of the probe-side facing-portion 51, the jaw-side facing-portion 55 can abut on the probe-side facing-portion 51 over the entire length in the longitudinal axis direction that is parallel to the longitudinal axis C.

Next, the function and advantageous effects of the ultrasonic treatment apparatus 1 and the ultrasonic probe 31 of the present embodiment are described. When a treatment target, such as a living body tissue, is treated by using the ultrasonic treatment apparatus 1, the jaw 11, the ultrasonic probe 31 and the sheath 40 are inserted into a body cavity. Then, in the state in which the jaw 11 is opened relative to the distal treatment section 33, the distal treatment section 33 is disposed at such a position that the treatment target can be grasped between the jaw 11 and distal treatment section 33. Here, the distal treatment section 33 is provided with the probe bend portion 37 which bends toward the first bend direction relative to the longitudinal axis C. In addition, in the probe bend portion 37, the position in the axis bend proximal ends (Q1~Q3), the extension direction of the cross-sectional center axis (M1~M3) becoming nonparallel to the longitudinal axis C at each of the axis bend proximal ends, is toward the proximal direction side, as the position therein is toward the first perpendicular direction that is the jaw opening direction. Besides, in the probe bend portion 37, the curvatures (R1~R3) in the cross-sectional center axes (M1~M3) become smaller, as the position therein is toward the first perpendicular direction that is the jaw opening direction. Since the distal treatment section 33 is formed in the above-described shape, the distal treatment section 33 can easily be made to reach such a position that the treatment target can be grasped between the jaw 11 and the distal treatment section 33.

Then, in the state in which the treatment target is positioned between the jaw 11 and the distal treatment section 33, the movable handle 7 is closed relative to the stationary handle 6. Thereby, the jaw 11 performs a closing motion relative to the distal treatment section 33, and the treatment target is grasped between the jaw 11 and distal treatment section 33. Since the distal treatment section 33 is formed in the above-described shape, the visibility of a surgeon is secured at a time of treatment in which the treatment target is grasped between the jaw 11 and the distal treatment section 33.

In addition, the jaw-side facing-portion 55 of the jaw 11 is bent in the first bend direction and second bed direction in the state in which the jaw-side facing-portion 55 is opposed to the probe-side facing-portion 51 of the distal treatment section 33, and is formed in the second bend shape which corresponds to the first bend shape of the probe-side facing-portion 51. Thus, in the state in which the treatment target is not disposed between the jaw 11 and distal treatment section 33, the jaw-side facing-portion 55 abuts on the probe-side facing-portion 51 over the entire length in the longitudinal axis direction that is parallel to the longitudinal axis C. By adopting the above structure, the treatment target is grasped between the jaw-side facing-portion 55 and probe-side facing-portion 51, with a uniform grasping force over the entire length in the longitudinal axis direction. In addition, since the jaw-side facing-portion 55 of the jaw 11 bends toward the first bend direction in accordance with the bending of the probe-side facing-portion 51 in the probe bend portion 37, the visibility of the surgeon is improved at a time of treatment in which the treatment target is grasped between the jaw 11 and the distal treatment section 33.

Then, by the energy operation being input by the energy operation input button 9, an ultrasonic generation current is supplied from the ultrasonic current supply section 16 to the ultrasonic vibrator 21, and an ultrasonic vibration occurs in the ultrasonic vibrator 21. The generated ultrasonic vibration is transmitted to the ultrasonic probe 31 via the horn member 23. In addition, in the ultrasonic probe 31, the ultrasonic vibration is transmitted to the distal treatment section 33 from the proximal direction toward the distal direction, and the ultrasonic probe 31 performs a longitudinal vibration with the vibration direction that is parallel to the longitudinal axis C. Since the distal treatment section 33 longitudinally vibrates in the state in which the treatment target is grasped between the jaw 11 and distal treatment section 33, frictional heat occurs between the distal treatment section 33 and the treatment target. By the frictional heat, the treatment target is coagulated and, at the same time, is cut.

The ultrasonic probe 31 is provided with the probe bend portion in which the center of gravity GB is located on the first bend direction side with respect to the longitudinal axis C. Thus, imprecise vibrations, such as a lateral vibration and a torsional vibration, occur in the ultrasonic probe 31 due to the transmission of the ultrasonic vibration, aside from the longitudinal vibration which is used in treatment. The effect of the abnormal vibrations increases as the distance (deviation) of the center of gravity GB of the probe bend portion 37 from the longitudinal axis C toward the first bend direction becomes greater. With the effect of the imprecise vibration increasing, the stability of the ultrasonic vibration in the ultrasonic probe 31 deteriorates. However, from the standpoint of the facility with which the distal treatment section 33 reaches the position where the treatment target can be grasped, and from the standpoint of the visibility of the surgeon at a time of treatment, a part of the probe bend portion 37 on the first perpendicular direction (jaw opening direction) side, in which the probe-side facing-portion 51 is located, needs to be formed in the above-described shape. Thus, in the first-perpendicular-direction-side part, the distance of the cross-sectional center of gravity (GB2) of the probe bend portion 37 from the longitudinal axis C toward the first bend direction increases (see FIG. 6).

Thus, in the present embodiment, the cross-sectional shape of the probe bend portion 37 in the cross sections perpendicular to the first perpendicular direction and the second perpendicular direction varies continuously along the first perpendicular direction and the second perpendicular direction. Thereby, the cross-sectional center of gravity (GB1~GB3) of the probe bend portion 37 is toward the second bend direction side, as it is from the first perpendicular direction (jaw opening direction) toward the second perpendicular direction (jaw closing direction). Since the position of the cross-sectional center of gravity (GB1~GB3) of the probe bend portion 37 shifts toward the second bend direction as a position in the cross sections is from the first perpendicular direction toward the second perpendicular direction, the distance of the cross-sectional center of gravity (GB3) of the probe bend portion 37 from the longitudinal axis C toward the first bend direction decreases in the second-perpendicular-direction-side part (see FIG. 7). Specifically, even in the case where the distance of the cross-sectional center of gravity (GB2) of the probe bend portion 37 from the longitudinal axis C toward the first bend direction increases in the first-perpendicular-direction-side part, the distance of the cross-sectional center of gravity (GB3) of the probe bend portion 37 from the longitudinal axis C in the first bend direction decreases in the second-perpendicular-direction-side part. Thereby, the distance of the center of gravity GB of the probe bend portion 37 from the longitudinal axis C toward the first bend direction decreases is not large.

Since the distance (deviation) of the center of gravity GB of the probe bend portion 37 from the longitudinal axis C toward the first bend direction does not increase, the effect of the imprecise vibrations on the longitudinal vibration is decreased. Since the effect of the imprecise vibrations decreases, the stability of the ultrasonic vibration in the ultrasonic probe 31 is secured. Thereby, the ultrasonic vibration is properly transmitted in the ultrasonic probe 31, and the treatment performance is secured in the above-described treatment using the ultrasonic vibration, such as ultrasonic coagulation-and-cutting.

Furthermore, at the time of treatment, the treatment target is grasped between the jaw-side facing-portion 55 and probe-side facing-portion 51, with a uniform grasping force over the entire length in the longitudinal axis direction. Therefore, the treatment performance in ultrasonic coagulation-and-cutting is improved.

As has been described above, in the present embodiment, it is possible to provide the ultrasonic probe 31 which is easily used by a surgeon, and secures stability of the ultrasonic vibration. In addition, it is possible to provide the ultrasonic treatment apparatus 1 including this ultrasonic probe 31.

Modifications of First Embodiment

Figure 17:
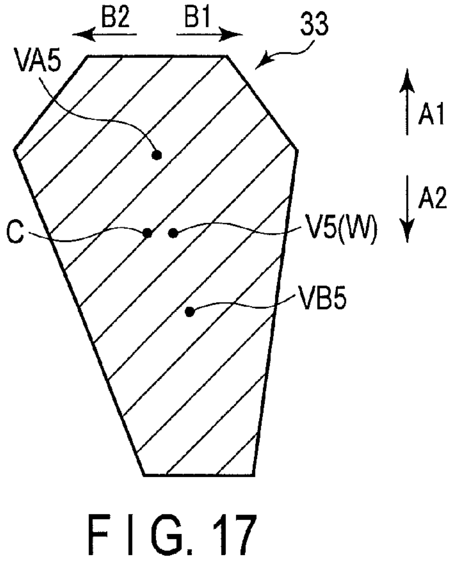
FIG. 17 is a cross-sectional view illustrating a cross section I5 in FIG. 15.
Figure 18:
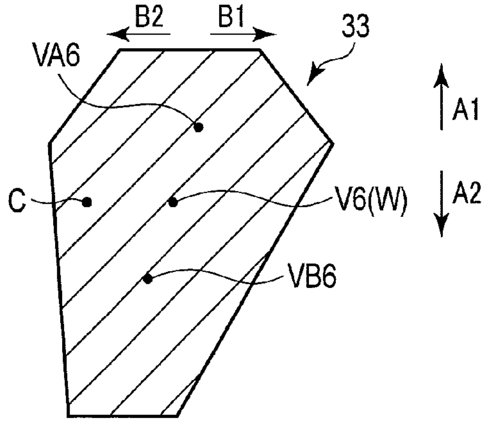
FIG. 18 is a cross-sectional view illustrating a cross section I6 in FIG. 15.
Figure 19:
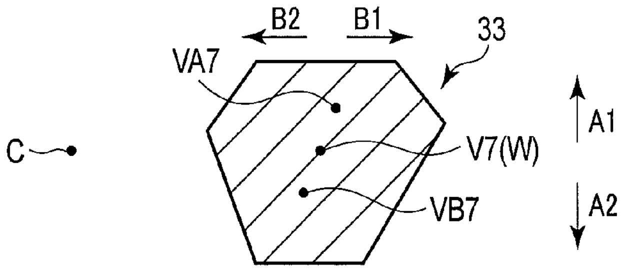
FIG. 19 is a cross-sectional view illustrating a cross section I7 in FIG. 15.

In the meantime, in the first embodiment, in each of the cross sections perpendicular to the center-of-gravity axis W, the second transverse cross-sectional half-part center of gravity VB2 does not deviate toward the first bend direction side with respect to the transverse cross-sectional center of gravity V, but it is not limited to this. For example, referring to FIG. 15 to FIG. 19, a first modification of the first embodiment is described. FIG. 15 is a view illustrating a structure of a distal treatment section 33 of the present modification. FIG. 16 to FIG. 19 are views illustrating the distal treatment section 33 by cross sections (transverse cross sections) perpendicular to the center-of-gravity axis W. FIG. 16 illustrates a cross section I4 in FIG. 15, FIG. 17 illustrates a cross section I5 in FIG. 15, FIG. 18 illustrates a cross section I6 in FIG. 15, and FIG. 19 illustrates a cross section I7 in FIG. 15. The cross-section I4 is a cross section on the proximal direction side with respect to the boundary D, and the cross section I5, cross section I6 and cross section I7 are cross sections on the distal direction side with respect to the boundary D. In addition, the cross section I6 is located on the distal direction side with respect to the cross section I5, and the cross section I7 is located on the distal direction side with respect to the cross section I6. Incidentally, the definitions of the transverse cross-sectional center of gravity V, the first transverse cross-sectional half-part center of gravity VA and the second transverse cross-sectional half-part center of gravity VB are the same as in the first embodiment.

In the cross section I4 illustrated in FIG. 16, since the cross section I4 is located on the proximal direction side with respect to the boundary D, the center-of-gravity axis W is coaxial with the longitudinal axis C, and the longitudinal axis C passes through a lateral cross-sectional center of gravity V4. In addition, in the first bend direction (direction of arrow B1 in FIG. 15 to FIG. 19) and the second bend direction (direction of arrow B2 in FIG. 15 to FIG. 19), a first lateral cross-sectional half-part center of gravity VA4 and a second lateral cross-sectional half-part center of gravity VB4 are not shifted from the center-of-gravity axis W (transverse cross-sectional center of gravity V4). In the meantime, although the cross-sectional shape of the probe main body portion 35, which is perpendicular to the longitudinal axis C (center-of-gravity axis W), is octagonal in the first embodiment, this cross-sectional shape is hexagonal in this modification.

In each of the cross section I5 illustrated in FIG. 17, cross section I6 illustrated in FIG. 18 and cross section I7 illustrated in FIG. 19, since the cross section is located on the distal direction side with respect to the boundary D, the transverse cross-sectional center of gravity (a corresponding one of V5~V7) is apart from the longitudinal axis C toward the first bend direction side. In addition, the distance from the longitudinal axis C to the transverse cross-sectional center of gravity V6 in the cross section I6 is greater than the distance from the longitudinal axis C to the transverse cross-sectional center of gravity V5 in the cross section I5. Besides, the distance from the longitudinal axis C to the transverse cross-sectional center of gravity V7 in the cross section I7 is greater than the distance from the longitudinal axis C to the transverse cross-sectional center of gravity V6 in the cross section I6.

In the present modification, in the cross section I5, the first lateral cross-sectional half-part center of gravity (VA5) is displaced toward the second bend direction side from the cross-sectional center of gravity (V5), and the second lateral cross-sectional half-part center of gravity (VB5) is shifted toward the first bend direction side from the cross-sectional center of gravity (V5). However, in each of the cross section I6 and the cross section I7, the first transverse cross-sectional half-part center of gravity (a corresponding one of VA6 and VA7) is displaced toward the first bend direction side from the cross-sectional center of gravity (a corresponding one of V6 and V7), and the second transverse cross-sectional half-part center of gravity (a corresponding one of VB6 and VB7) is shifted toward the second bend direction side from the cross-sectional center of gravity (a corresponding one of V6 and V7). Thus, in each of the cross section I6 and cross section I7, the distance from the longitudinal axis C to the first transverse cross-sectional half-part center of gravity (a corresponding one of VA6 and VA7) increases, but the distance from the longitudinal axis C to the second transverse cross-sectional half-part center of gravity (a corresponding one of VB6 and VB7) toward the first bend direction is small. In addition, in the cross section I5, although the second transverse cross-sectional half-part center of gravity VB5 is displaced toward the first bend direction side from the cross-sectional center of gravity V5, the distance from the longitudinal axis C to the cross-sectional center of gravity V5 is smaller than in the cross section I6 and cross section I7. Accordingly, in the cross section I5, too, the distance in the first bend direction from the longitudinal axis C to the second lateral cross-sectional half-part center of gravity VB5 decreases.

As described above, in the present modification, like the first embodiment, in the probe bend portion 37, the distance of the second transverse cross-sectional half-part center of gravity VB, which is the half-part center of gravity on the second perpendicular direction side with respect to the transverse cross-sectional center of gravity V, from the longitudinal axis C toward the first bend direction becomes small. Thereby, the distance of the center of gravity GB of the probe bend portion 37 from the longitudinal axis C toward the first bend direction does not increase. Like the first embodiment, since the distance (deviation) of the center of gravity GB of the probe bend portion 37 from the longitudinal axis C in the first bend direction is not large, the effect of imprecise vibrations on the longitudinal vibration is decreased.

Besides, in the first embodiment, over the entire dimension in the first perpendicular direction and the second perpendicular direction, the cross-sectional shape of the probe bend portion 37 in the cross section perpendicular to the first perpendicular direction and the second perpendicular direction is the shape bending toward the first end direction relative to the longitudinal axis C. However, it is not limited to this. For example, referring to FIG. 20 and FIG. 21, a description is given of a second modification of the first embodiment, which differs from the first embodiment in the cross-sectional shape of the probe bend portion 37 in the cross section perpendicular to the first perpendicular direction and the second perpendicular direction.

FIG. 20 and FIG. 21 are views illustrating the distal treatment section 33 by cross sections perpendicular to the first perpendicular direction and the second perpendicular direction. Here, FIG. 20 is a cross section on the first perpendicular direction side (jaw opening direction side) with respect to the longitudinal axis C, and FIG. 21 is a cross section on the second perpendicular direction side (jaw closing direction side) with respect to the longitudinal axis C.

As illustrated in FIG. 20 and FIG. 21, in each of the cross sections perpendicular to the first perpendicular direction and the second perpendicular direction of the distal treatment section 33, like the first embodiment, a cross-sectional center axis (a corresponding one of M4 and M5), which passes through the center position of the ultrasonic probe 31 in the first bend direction (direction of arrow B1 in FIG. 20 and FIG. 21) and the second bend direction (direction of arrow B2 in FIG. 20 and FIG. 21), is defined. In addition, in each of the cross sections perpendicular to the first perpendicular direction and the second perpendicular direction, an axis bend proximal end (a corresponding one of Q4 and Q5), at which the extending direction of the cross-sectional center axis (a corresponding one of M4 and M5) becomes nonparallel to the longitudinal axis C, is located in the probe bend portion 37. The position in the axis bend proximal ends (Q4, Q5) in the longitudinal axis direction parallel to the longitudinal axis C varies along the first perpendicular direction and the second perpendicular direction.

In the cross section of FIG. 20 which is located on the first perpendicular direction side with respect to the longitudinal axis C, the cross-sectional center axis M4 bends toward the first bend direction in a part on the distal direction side with respect to the axis bend proximal end (bend start position) Q4. In addition, in the cross section of FIG. 21 which is located on the second perpendicular direction side with respect to the longitudinal axis C, the cross-sectional center axis M5 bends toward the second bend direction at the axis bend proximal end (bend start position) Q5. Then, from the axis bend proximal end Q5 to a bend direction change position S5, the cross-sectional center axis M5 extends in the state in which the cross-sectional center axis M5 bends toward the second bend direction relative to the longitudinal axis C. In the part on the distal direction side from the bend direction change position S5, the cross-sectional center axis M5 bends toward the first bend direction.

In the present modification, like the first embodiment, in each of the cross sections perpendicular to the first perpendicular direction and the second perpendicular direction, in a part on the proximal direction side with respect to the axis bend proximal end (a corresponding one of Q4 and Q5) of the probe bend portion 37, the cross-sectional center axis (a corresponding one of M4 and M5) is provided to extend in parallel to the longitudinal axis C. In addition, in the case where, among the cross sections perpendicular to the first perpendicular direction and the second perpendicular direction, the cross section, in which the axis bend proximal end is located most proximally, is set to be the boundary-defining cross section, the boundary D between the probe main body portion 35 and probe bend portion 37 in the longitudinal axis direction coincides with the axis bend proximal end of the cross-sectional center axis in the boundary-defining cross section.

As described above, in the present modification, too, the cross-sectional shape of the probe bend portion 37 in the cross sections perpendicular to the first perpendicular direction and the second perpendicular direction varies continuously along the first perpendicular direction and the second perpendicular direction. The cross-sectional shape of the probe bend portion 37 varies along the first perpendicular direction and the second perpendicular direction, and thereby the position of the cross-sectional center of gravity (GB4, GB5) of the probe bend portion 37 varies along the first perpendicular direction and the second perpendicular direction. In this modification, too, the cross-sectional center of gravity (GB4, GB5) of the probe bend portion 37 lies toward the second bend direction side, as it is from the first perpendicular direction (jaw opening direction) toward the second perpendicular direction (jaw closing direction). Accordingly, the cross-sectional center of gravity GB4 of the probe bend portion 37 in the cross section of FIG. 20 is located on the first bend direction side with respect to the cross-sectional center of gravity GB5 of the probe bend portion 37 in the cross section of FIG. 21. In addition, in the cross section of FIG. 21 which is located on the second perpendicular' direction side with respect to the longitudinal axis C, the cross-sectional center of gravity GB5 of the probe bend portion 37 is located on the second bend direction side with respect to the longitudinal axis C.

As described above, the position of the cross-sectional center of gravity (GB4, GB5) of the probe bend portion 37 shifts toward the second bend direction, as the position in the cross sections is from the first perpendicular direction toward the second perpendicular direction. Thus, in the second-perpendicular-direction-side part, the cross-sectional center of gravity (GB5) of the probe bend portion 37 is located on the second bend direction side with respect to the longitudinal axis C. Thereby, even in the case where the distance of the cross-sectional center of gravity (GB4) of the probe bend portion 37 from the longitudinal axis C toward the first bend direction increases in the first-perpendicular-direction-side part, the distance of the cross-sectional center of gravity GB of the probe bend portion 37 from the longitudinal axis C toward the first bend direction does not increase. Since the distance (deviation) of the center of gravity GB of the probe bend portion 37 from the longitudinal axis C toward the first bend direction is not large, the effect of the imprecise vibrations on the longitudinal vibration is decreased. Therefore, the stability of the ultrasonic vibration in the ultrasonic probe 31 is secured.

Besides, as illustrated in FIG. 22 as a third modification of the first embodiment, the dimension of the probe bend portion 37 in the first perpendicular direction and the second perpendicular direction may vary in accordance with a variation of the position in the longitudinal axis direction that is parallel to the longitudinal axis C. In the present embodiment, the probe bend portion 37 is provided with a dimension varying portion 61 the dimension of which in the first perpendicular direction (direction of arrow A1 in FIG. 22) and the second perpendicular direction (direction of arrow A2 in FIG. 22) varies in accordance with a variation of the position in the longitudinal axis direction. In the dimension varying portion 61, the dimension becomes smaller in the first perpendicular direction and second perpendicular direction of the probe bend portion 37, as the position is from the proximal direction toward the distal direction side.

FIG. 23 and FIG. 24 are views illustrating the distal treatment section 33 by cross sections perpendicular to the first perpendicular direction and the second perpendicular direction. Here, FIG. 23 is a cross section on the first perpendicular direction side (jaw opening direction side) with respect to the longitudinal axis C, and FIG. 24 is a cross section on the second perpendicular direction side (jaw closing direction side) with respect to the longitudinal axis C.

As illustrated in FIG. 23 and FIG. 24, in each of the cross sections perpendicular to the first perpendicular direction and the second perpendicular direction of the distal treatment section 33, like the first embodiment, a cross-sectional center axis (a corresponding one of M6 and M7), which passes through the center position of the ultrasonic probe 31 in the first bend direction (direction of arrow B1 in FIG. 23 and FIG. 24) and the second bend direction (direction of arrow B2 in FIG. 23 and FIG. 24), is defined. Like the cross-sectional center axes (M1~M3) of the first embodiment, in the cross section of FIG. 23 on the first perpendicular direction side with respect to the longitudinal axis C, a distal end E6 of the cross-sectional center axis M6 is located on the distal surface 38 that forms the distal end of the ultrasonic probe 31. However, in the present modification, since the dimension varying portion 61 is provided, a distal end E7 of the cross-sectional center axis M7, which is defined in the cross section of FIG. 24 on the second perpendicular direction side with respect to the longitudinal axis C, is located on the proximal direction side with respect to the distal surface 38. Specifically, the cross-sectional center axis M7 does not extend up to the distal surface 38. In the present modification, in the second-perpendicular-direction-side part, the cross-sectional center axis (M7) is not provided to extend up to the distal surface 38. Thus, the distal surface center line L0, which passes through the center position of the distal surface 38 in the first bend direction and the second bend direction, is formed by making continuous each cross-sectional center axis (M6) having the distal end (E6) located on the distal surface 38.

In addition, in the present modification, too, the cross-sectional shape of the probe bend portion 37 in the cross sections perpendicular to the first perpendicular direction and the second perpendicular direction varies continuously along the first perpendicular direction and the second perpendicular direction. The cross-sectional shape of the probe bend portion 37 varies along the first perpendicular direction and the second perpendicular direction, and thereby the position of the cross-sectional center of gravity (GB6, GB7) of the probe bend portion 37 varies along the first perpendicular direction and the second perpendicular direction. In this modification, too, the cross-sectional center of gravity (GB6, GB7) of the probe bend portion 37 lies toward the second bend direction side, as the position in the cross sections is from the first perpendicular direction (jaw opening direction) toward the second perpendicular direction (jaw closing direction).

Besides, in the first embodiment, the cross section of the distal treatment section 33, which is perpendicular to the longitudinal axis C, is octagonal, but it is not restricted to this. Referring to FIG. 25, a description is given of a distal treatment section 33 of an ultrasonic probe 31 according to a fourth modification of the first embodiment. FIG. 25 illustrates the distal treatment section 33 and the jaw 11 by a cross section perpendicular to the longitudinal axis C. In addition, FIG. 25 illustrates a cross section on the proximal direction side with respect to the boundary D. As illustrated in FIG. 25, in the present modification, like the first embodiment, the distal treatment section 33 is provided with a probe-side facing-portion 51 which faces to the jaw 11 in the state in which the probe-side opposed-portion 51 faces in the first perpendicular direction (direction of arrow A1 in FIG. 25) that is the jaw opening direction. In addition, the probe-side facing-portion 51 is provided with a probe-side abutment surface 52 and inclined facing-surfaces 53A and 53B.

Here, a first inclination direction and a second inclination direction are defined, the first inclination direction being inclined by a first angle $\alpha 1$, which is an acute angle, from the second perpendicular direction (direction of arrow A2 in FIG. 25) that is the jaw closing direction toward the second bend direction (direction of arrow B2 in FIG. 25), and the second inclination direction being inclined by a second angle $\alpha 2$, which is an acute angle, from the second perpendicular direction toward the first bend direction (direction of arrow B1 in FIG. 25). The distal treatment section 33 includes a first inclined surface 62A which is provided to extend from the inclined facing-surface (first inclined facing-surface) 53A of the probe-side facing-portion 51 toward the first inclination direction, and a second inclined surface 62B which is provided to extend from the inclined facing-surface (second inclined facing-surface) 53B of the probe-side facing-portion 51 toward the second inclination direction. The first inclined surface 62A is continuous with the second perpendicular direction side of the inclined opposed-surface 53A in the state in which the first inclined surface 62A faces toward the first bend direction. The second inclined surface 62B is continuous with the second perpendicular direction side of the inclined opposed-surface 53B in the state in which the second inclined surface 62B faces toward the second bend direction. In addition, the first inclined surface 62A and the second inclined surface 62B are continuous via a joining surface 63 which faces toward the second perpendicular direction.

By configuring the distal treatment section 33 as described above, a living body tissue does not come in contact with the distal treatment section 33, in the parts other than a treatment target which is grasped between the jaw-side facing-portion 55 and the probe-side facing-portion 51. In other words, a living body tissue does not come in contact with the parts (i.e. first inclined surface 62A, second inclined surface 62B and joining surface 63) other than the probe-side facing-portion 51 that comes in contact with the treatment target. Since the ultrasonic vibration is transmitted as energy, heat occurs in the distal treatment section 33, and the distal treatment section 33 has high temperatures. Since the living tissue does not come in contact with the parts other than the probe-side facing-portion 51 of the distal treatment section 33, thermal damage to the living body tissue at the parts other than the treatment target can effectively be prevented.

Second Embodiment

Figure 26:
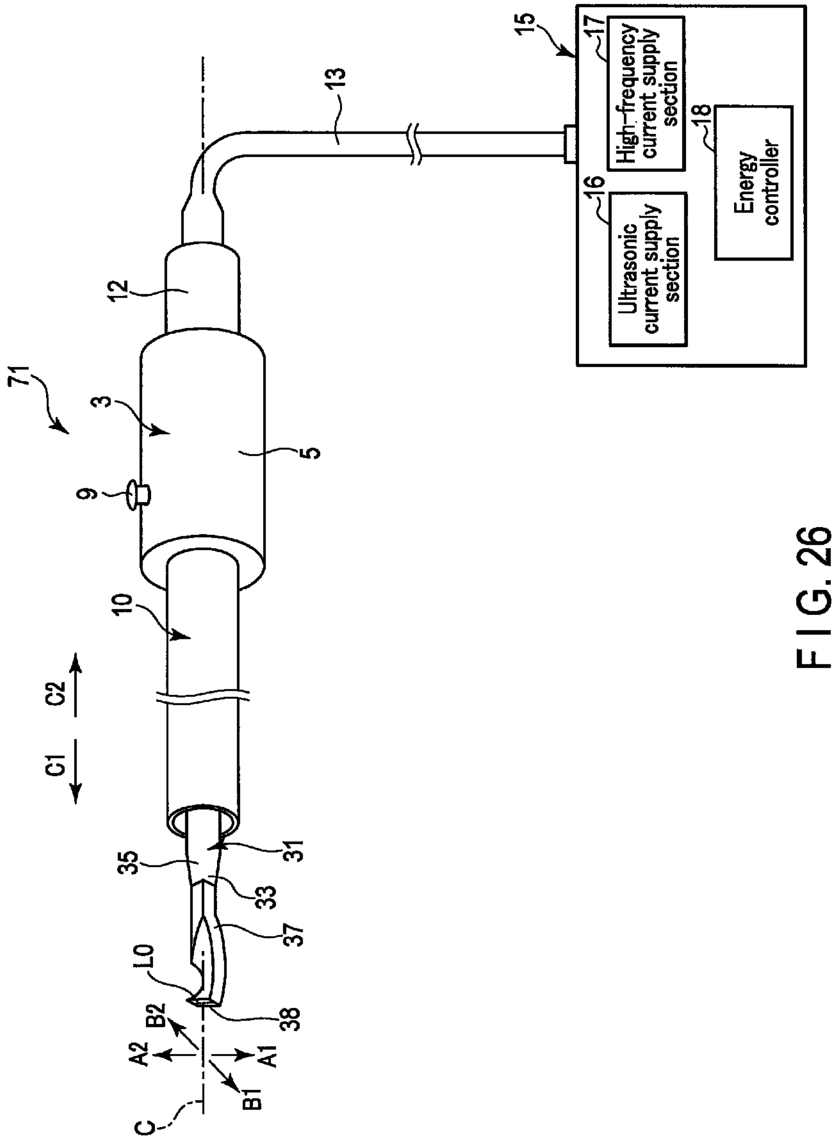
FIG. 26 is a schematic view illustrating a structure of an ultrasonic treatment apparatus according to a second embodiment.

Besides, referring to FIG. 26 to FIG. 28, a description is given of a second embodiment in which the ultrasonic probe 31 is applied to an ultrasonic treatment apparatus 71 which is different from the ultrasonic treatment apparatus 1 that is the ultrasonic coagulation-and-cutting apparatus. Incidentally, in the description below, the same parts as in the first embodiment are denoted by like reference numerals, and a description thereof is omitted. FIG. 26 is a view illustrating a structure of the ultrasonic treatment apparatus 71. The ultrasonic treatment apparatus 71 is an ultrasonic resection apparatus which resets a treatment target such as a living body tissue, by using an ultrasonic vibration and a high-frequency current. As illustrated in FIG. 26, in the ultrasonic treatment device 71, like the ultrasonic treatment apparatus 1 of the first embodiment, there are provided a holding unit 3, a vibrator case 12, a sheath 10 and an ultrasonic probe 31.

In addition, in an inside of the oscillator case 12, an ultrasonic vibrator 21 and a horn member 23 are provided, and the ultrasonic vibration occurring in the ultrasonic transducer 21 is transmitted to the ultrasonic probe 31 via the horn member 23.

Furthermore, a distal treatment section 33 of the ultrasonic probe 31 is provided in a state in which the distal treatment section 33 projects from the distal end of the sheath 10 toward the distal direction (direction of arrow C1 in FIG. 26).

In the present embodiment, however, the holding unit 3 is not provided with a stationary handle 6, a movable handle 7 or a rotary operation knob 8. In addition, an energy operation input button 9 that is an energy operation input section is attached to a cylindrical case portion 5. The ultrasonic treatment apparatus 71 is not provided with a jaw 11. Besides, the control unit 15 includes a high-frequency current supply section 17 in addition to the ultrasonic current supply section 16 and the energy controller 18. The high-frequency current supply section 17 is a electric power supply which is provided, for example, in an energy generator. In this embodiment, an electric wiring line (not shown), which is different from the electric wiring lines 25A and 25B, is provided to extend in the inside of the cable 13. One end of this electric wiring line is connected to the horn member 23, and the other end thereof is connected to the high-frequency current supply section 17.

By an energy operation being input in the energy operation input button 9, the energy controller 18 supplies an ultrasonic generation current from the ultrasonic current supply section 16 to the ultrasonic vibrator 21, and supplies a high-frequency current from the high-frequency current supply section 17. By the ultrasonic generation current being supplied to the ultrasonic vibrator 21, an ultrasonic vibration occurs in the ultrasonic oscillator 21, and the generated ultrasonic vibration is propagated to the ultrasonic probe 31 via the horn member 23. Then, in the ultrasonic probe 31, the ultrasonic vibration is transmitted to the distal treatment section 33 from the proximal direction toward the distal direction, and the ultrasonic probe 31 performs the longitudinal vibration with the vibration direction that is parallel to the longitudinal axis C. In addition, a high-frequency current is transmitted to the distal treatment section 33 via the horn member 23 and the ultrasonic probe 31. Then, the high-frequency current is discharged in the distal treatment section 33. A treatment target is resected by bringing the distal treatment section 33, which discharges the high-frequency current and longitudinally vibrates, into contact with the treatment target such as a living body tissue.

FIG. 27 and FIG. 28 are views illustrating the distal treatment section 33 by cross sections perpendicular to the first perpendicular direction and the second perpendicular direction. Here, FIG. 27 is a cross section on the first perpendicular direction (direction of arrow A1 in FIG. 26) side with respect to the longitudinal axis C, and FIG. 28 is a cross section on the second perpendicular direction (direction of arrow A2 in FIG. 26) side with respect to the longitudinal axis. At a time of treatment, the surgeon performs visual recognition from the first perpendicular direction. As illustrated in FIG. 27 and FIG. 28, in the present embodiment, like the first embodiment, the ultrasonic probe 31 includes a probe main body portion 35 and a probe bend portion 37. In the present embodiment, however, the bend state of the probe bend portion 37 in the first bend direction (direction of arrow B1 in FIG. 27 and FIG. 28) and the second bend direction (direction of arrow B2 in FIG. 27 and FIG. 28) differs from that in the first embodiment.

In each of the cross sections perpendicular to the first perpendicular direction and the second perpendicular direction of the distal treatment section 33, like the first embodiment, a cross-sectional center axis (a corresponding one of M8 and M9), which passes through the center position of the ultrasonic probe 31 in the first bend direction and the second bend direction, is defined. In addition, in each of the cross sections perpendicular to the first perpendicular direction and the second perpendicular direction, an axis bend proximal end (a corresponding one of Q8 and Q9), at which the extending direction of the cross-sectional center axis (a corresponding one of M8 and M9) becomes nonparallel to the longitudinal axis C, is located in the probe bend portion 37. In the present embodiment, the position in the axis bend proximal ends (Q8, Q9) in the longitudinal axis direction parallel to the longitudinal axis C varies along the first perpendicular direction and the second perpendicular direction. Specifically, the position in the axis bend proximal ends (Q8, Q9) lies toward the distal direction side, as the position therein is from the first perpendicular direction toward the second perpendicular direction. Accordingly, the axis bend proximal end (bend start position) Q8 in the cross section of FIG. 27 is located on the proximal direction side with respect to the axis bend proximal end (bend start position) Q9 in the cross section of FIG. 28.

In each of the cross sections perpendicular to the first perpendicular direction and the second perpendicular direction, the cross-sectional center axis (a corresponding one of M8 and M9) bends toward the first bend direction at the axis bend proximal end (a corresponding one of Q8 and Q9). Then, in each of the cross sections perpendicular to the first perpendicular direction and the second perpendicular direction, from the axis bend proximal end (a corresponding one of Q8 and Q9) to a bend direction change position (a corresponding one of S8 and S9), the cross-sectional center axis (a corresponding one of M8 and M9) extends in the state in which the cross-sectional center axis bends toward the first bend direction relative to the longitudinal axis C. The bend direction change positions (S8, S9) in the longitudinal axis direction, which is parallel to the longitudinal axis C, vary along the first perpendicular direction and second perpendicular direction. Specifically, the bend direction change position (S8, S9) lies toward the distal direction side, relative to a direction from the first perpendicular direction toward the second perpendicular direction. The dimension toward the first bend direction from the longitudinal axis C to the bend direction change position (S8, S9) does not vary over the entire dimension in the first perpendicular direction and the second perpendicular direction in the part on the distal end direction side from the bend direction change positions (S8, S9), the cross-sectional center axes (M8, M9) bend toward the second bend direction.

In the present embodiment, too, the distal end (E8, E9) of each cross-sectional center axis (M8, M9) is located at the distal surface 38. The position of the distal end (E8, E9) of each cross-sectional center axis (M8, M9) in the first bend direction and the second bend direction agrees with the longitudinal axis C. Accordingly, in this embodiment, the distal surface center line L0 intersects at right angles with the longitudinal axis C. In addition, in the case where, among the cross sections perpendicular to the first perpendicular direction and the second perpendicular direction, the cross section, in which the axis bend proximal end is located most proximally, is set to be the boundary-defining cross section, the cross section (contact surface) passing through the first-perpendicular-direction-side end of the probe bend portion 37 becomes the boundary-defining cross section. The boundary D between the probe main body portion 35 and probe bend portion 37 in the longitudinal axis direction coincides with the axis bend proximal end of the cross-sectional center axis in the boundary-defining cross section.

In each of the cross sections perpendicular to the first perpendicular direction and the second perpendicular direction, in the part on the distal direction side with respect to the axis bend proximal end (a corresponding one of Q8 and Q9), the cross-sectional center axis (a corresponding one of M8 and M9) bends with a curvature (a corresponding one of R8 and R9) in the first bend direction and the second bend direction. The curvature (R8, R9) of the cross-sectional center axis (M8, M9) varies along the first perpendicular direction and second perpendicular direction. Specifically, the curvature (R8, R9) of the cross-sectional center axis (M8, M9) becomes greater, relative to a direction from the first perpendicular direction toward the second perpendicular direction. Accordingly, the curvature R8 of the cross-sectional center axis M8 in the cross section of FIG. 27 is less than the curvature R9 of the cross-sectional center axis M9 in the cross section of FIG. 28.

In the present embodiment, too, since the probe bend portion 37 is formed as described above, the cross-sectional shape of the probe bend portion 37 in the cross sections perpendicular to the first perpendicular direction and the second perpendicular direction varies continuously along the first perpendicular direction and the second perpendicular direction. In the present embodiment, the probe bend portion 37 is formed in a spatula shape. The cross-sectional shape of the probe bend portion 37 varies along the first perpendicular direction and the second perpendicular direction, and thereby the position of the cross-sectional center of gravity (GB8, GB9) of the probe bend portion 37 varies along the first perpendicular direction and the second perpendicular direction. In this embodiment, too, the cross-sectional center of gravity (GB8, GB9) of the probe bend portion 37 is toward the second bend direction side, relative to the direction from the first perpendicular direction toward the second perpendicular direction. Accordingly, the cross-sectional center of gravity GB9 of the probe bend portion 37 in the cross section of FIG. 28 is located on the second bend direction side with respect to the cross-sectional center of gravity GB8 of the probe bend portion 37 in the cross section of FIG. 27.

At a time of treatment, the surgeon performs visual recognition from the first perpendicular direction. Thus, from the standpoint of the visibility of the surgeon at the time of treatment, in the probe bend portion 37, in the part on the first perpendicular direction side, it is necessary to increase the dimension of the axis bend proximal end (Q8) of the cross-sectional center axis (M8) from the distal surface 38 in the longitudinal axis direction, and to decrease the curvature (R8) of the cross-sectional center axis (M8). Thus, in the first-perpendicular-direction-side part, the distance of the cross-sectional center of gravity (GB8) of the probe bend portion 37 from the longitudinal axis C toward the first bend direction increases (see FIG. 27).

In the present embodiment, however, the position of the cross-sectional center of gravity (GB8, GB9) of the probe bend portion 37 shifts toward the second bend direction, as the position in the cross sections is from the first perpendicular direction toward the second perpendicular direction. Thus, in the part on the second perpendicular direction side, the distance of the cross-sectional center of gravity (GB9) of the probe bend portion 37 from the longitudinal axis C toward the first bend direction decreases (see FIG. 28). Thereby, even in the case where the distance of the cross-sectional center of gravity (GB8) of the probe bend portion 37 from the longitudinal axis C toward the first bend direction increases in the first-perpendicular-direction-side part, the distance of the cross-sectional center of gravity GB of the probe bend portion 37 from the longitudinal axis C toward the first bend direction is not large. Since the distance (deviation) of the center of gravity GB of the probe bend portion 37 from the longitudinal axis C in the first bend direction does not increase, the effect of imprecise vibrations on the longitudinal vibration is decreased. Therefore, the stability of the ultrasonic vibration in the ultrasonic probe 31 is secured.

Modification of Second Embodiment

In the meantime, in the ultrasonic resection apparatus, such as the ultrasonic treatment apparatus 71, in which the jaw 11 is not provided, the probe bend portion 37 of the ultrasonic probe 31 may be formed in any one of the shapes in the first embodiment and the first to third modifications of the first embodiment. In addition, the probe bend portion 37 of the ultrasonic probe 31 may be formed in a hook shape bending in the first bend direction and second bend direction. Even when the probe bend portion 37 is formed in the hook shape, the cross-sectional shape of the probe bend portion 37 in the cross sections perpendicular to the first perpendicular direction and second perpendicular direction varies continuously along the first perpendicular direction and second perpendicular direction. In addition, the cross-sectional center of gravity of the probe bend portion 37 is toward the second bend direction side, as the position in the cross sections is from the first perpendicular direction toward the second perpendicular direction.

Other Modifications

From the above-described first embodiment including the modifications and the second embodiment including the modification, an ultrasonic probe 31 includes a probe main body portion 35 which extends along the longitudinal axis C with the longitudinal axis being an axial center, and transmits an ultrasonic vibration along the longitudinal axis C from a proximal direction (C2) toward a distal direction (C1); and a probe bend portion 37 which is provided on the distal direction (C1) side with respect to the probe main body portion 35. When one direction perpendicular to the longitudinal axis C is set to be a first bend direction (B1) and an opposite side to the first bend direction (B1) is set to be a second bend direction (B2), the probe bend portion 37 bends relative to the probe main body portion 35 in the first bend direction (B1) and the second bend direction (B2) in a state in which a center of gravity GB of the probe bend portion 37 is located on the first bend direction (B1) side with respect to the longitudinal axis C. When one side of a direction, which is perpendicular to the longitudinal axis C and is perpendicular to the first bend direction (B1) and the second bend direction (B2), is set to be a first perpendicular direction (A1) and an opposite side to the first perpendicular direction (A1) is set to be a second perpendicular direction (A2), a cross-sectional shape of the probe bend portion 37 in a cross section perpendicular to the first perpendicular direction (A1) and the second perpendicular direction (A2) varies continuously along the first perpendicular direction (A1) and second perpendicular direction (A2) in a state in which a cross-sectional center of gravity (GB1~GB3; GB4, GB5; GB6, GB7; GB8, GB9) of the probe bend portion 37 in the cross section perpendicular to the first perpendicular direction (A1) and the second perpendicular direction (A2) lies toward the second bend direction (B2) side, as it is from the first perpendicular direction (A1) toward the second perpendicular direction (A2).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe comprising:

a probe main body portion which extends along a longitudinal axis of the probe main body with the longitudinal axis being an axial center, and which is configured to transmit an ultrasonic vibration along the longitudinal axis from a proximal direction toward a distal direction; and a probe bend portion which is provided on the distal direction side with respect to the probe main body portion, when one direction perpendicular to the longitudinal axis is set to be a first bend direction and an opposite side to the first bend direction is set to be a second bend direction, the probe bend portion bending relative to the probe main body portion in the first bend direction and the second bend direction in a state in which a center of gravity is located on a first bend direction side with respect to the longitudinal axis, the probe bend portion being configured such that, when one side of a direction, which is perpendicular to the longitudinal axis and is perpendicular to the first bend direction and the second bend direction, is set to be a first perpendicular direction and an opposite side to the first perpendicular direction is set to be a second perpendicular direction, a cross-sectional shape of the probe bend portion in a cross section perpendicular to the first perpendicular direction and the second perpendicular direction varies continuously along the first perpendicular direction and the second perpendicular direction in a state in which a cross-sectional center of gravity of the probe bend portion in the cross section perpendicular to the first perpendicular direction and the second perpendicular direction lies toward the second bend direction side, as it is from the first perpendicular direction toward the second perpendicular direction.

2. The ultrasonic probe of claim 1, wherein, when a cross-sectional center axis, which passes through a center position of the ultrasonic probe in the first bend direction and the second bend direction, is defined in the cross section perpendicular to the first perpendicular direction and second perpendicular direction, the probe bend portion bends toward the first bend direction in a state in which a curvature of the cross-sectional center axis becomes larger, as it is from the first perpendicular direction toward the second perpendicular direction, and the probe bend portion is configured such that an axis bend proximal end, at which an extending direction of the cross-sectional center axis becomes nonparallel to the longitudinal axis, lies toward the distal direction side, as it is from the first perpendicular direction toward the second perpendicular direction.

3. The ultrasonic probe of claim 1, wherein the probe bend portion includes a distal surface which forms a distal end of the ultrasonic probe, when a distal surface center line, which passes through a center position of the ultrasonic probe in the first bend direction and the second bend direction is defined on the distal surface, the distal surface center line being parallel to the first perpendicular direction and the second perpendicular direction.

4. An ultrasonic treatment apparatus comprising:

the ultrasonic probe of claim 1;

a sheath which extends along the longitudinal axis, and through which the ultrasonic probe is inserted; and a jaw pivotably attached to the sheath, wherein the ultrasonic probe includes a distal treatment section in which the probe bend portion is located, and which projects from the sheath toward the distal direction, the jaw performing an opening motion or a closing motion relative to the distal treatment section in a state in which the first perpendicular direction is a jaw opening direction and the second perpendicular direction is a jaw closing direction.

5. The ultrasonic treatment apparatus of claim 4, wherein the distal treatment section includes a probe-side facing-portion which faces to the jaw in a state in which the probe-side facing-portion faces toward the first perpendicular direction, the probe-side facing-portion being configured to form a first bend shape by bending in the first bend direction and the second bend direction in the probe bend portion, and the jaw includes a jaw-side facing-portion which faces to the probe-side facing-portion in a state in which the jaw-side facing-portion faces toward the second perpendicular direction, the jaw-side facing-portion being able to abut on the probe-side facing-portion in a state in which the jaw is closed relative to the distal treatment section, and being configured to form a second bend shape, which corresponds to the first bend shape, by bending in the first bend direction and the second bend direction in a state in which the jaw-side facing-portion faces to the probe-side facing-portion.

6. The ultrasonic treatment apparatus of claim 4, wherein the distal treatment section includes:

a probe-side facing-portion which faces to the jaw in a state in which the probe-side facing-portion faces toward the first perpendicular direction;

a first inclined surface being continuous with the second perpendicular direction side of the probe-side facing-portion in a state in which the first inclined surface faces toward the first bend direction, and extending from the probe-side facing-portion toward a first inclination direction that is inclined by a first angle, which is an acute angle, from the second perpendicular direction toward the second bend direction;

a second inclined surface being continuous with the second perpendicular direction side of the probe-side facing-portion in a state in which the second inclined surface faces toward the second bend direction, and extending from the probe-side facing-portion toward a second inclination direction that is inclined by a second angle, which is an acute angle, from the second perpendicular direction toward the first bend direction; and a joining surface configured to make continuous the first inclined surface and the second inclined surface in a state in which the joining surface faces toward the second perpendicular direction.

* * * * *